United States Patent
Lincecum et al.

(10) Patent No.: US 12,275,793 B2
(45) Date of Patent: *Apr. 15, 2025

(54) ANTI-CD40L ANTIBODIES AND METHODS FOR TREATING CD40L-RELATED DISEASES OR DISORDERS

(71) Applicant: ALS Therapy Development Institute, Watertown, MA (US)

(72) Inventors: John M. Lincecum, Jamaica Plain, MA (US); Bingbing Jiang, Brighton, MA (US); Steven N. Perrin, Newbury, MA (US); Alan Gill, Reading, MA (US); Cynthia A. Gill, Reading, MA (US); Fernando G. Vieira, Boston, MA (US)

(73) Assignee: ALS THERAPY DEVELOPMENT INSTITUTE, Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/341,202

(22) Filed: Jun. 26, 2023

(65) Prior Publication Data

US 2024/0043549 A1  Feb. 8, 2024

Related U.S. Application Data

(60) Division of application No. 17/322,486, filed on May 17, 2021, now Pat. No. 11,692,040, which is a division of application No. 15/931,315, filed on May 13, 2020, now Pat. No. 11,014,990, which is a division of application No. 16/125,317, filed on Sep. 7, 2018, now Pat. No. 10,683,356, which is a division of application No. 15/667,477, filed on Aug. 2, 2017, now Pat. No. 10,106,618, which is a continuation of application No. PCT/US2016/016165, filed on Feb. 2, 2016.

(60) Provisional application No. 62/111,261, filed on Feb. 3, 2015.

(51) Int. Cl.
| | | |
|---|---|---|
| *A61K 39/00* | (2006.01) | |
| *A61K 39/395* | (2006.01) | |
| *A61K 45/06* | (2006.01) | |
| *C07K 16/28* | (2006.01) | |

(52) U.S. Cl.
CPC ...... *C07K 16/2875* (2013.01); *A61K 39/3955* (2013.01); *A61K 45/06* (2013.01); *C07K 2317/24* (2013.01); *C07K 2317/52* (2013.01); *C07K 2317/71* (2013.01); *C07K 2317/76* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,474,771 | A | 12/1995 | Lederman et al. |
| 5,637,481 | A | 6/1997 | Ledbetter et al. |
| 5,851,795 | A | 12/1998 | Linsley et al. |
| 5,961,974 | A | 10/1999 | Armitage et al. |
| 5,962,406 | A | 10/1999 | Armitage et al. |
| 6,001,358 | A | 12/1999 | Black et al. |
| 6,328,964 | B1 | 12/2001 | Noelle et al. |
| 6,340,459 | B1 | 1/2002 | Yellin et al. |
| 6,376,459 | B1 | 4/2002 | Aruffo et al. |
| 6,451,310 | B1 | 9/2002 | Lederman et al. |
| 6,838,261 | B1 | 1/2005 | Siegall et al. |
| 7,070,777 | B1 | 7/2006 | Lederman et al. |
| 7,169,389 | B2 | 1/2007 | Di Padova et al. |
| 7,173,046 | B2 | 2/2007 | Zheng et al. |
| 7,547,438 | B2 | 6/2009 | Thomas et al. |
| 7,563,443 | B2 | 7/2009 | Grant et al. |
| 7,647,438 | B1 | 1/2010 | Norrie et al. |
| 7,863,419 | B2 | 1/2011 | Taylor et al. |
| 8,293,237 | B2 | 10/2012 | Burkly et al. |
| 8,435,514 | B2 | 5/2013 | Perrin et al. |
| 8,647,625 | B2 | 2/2014 | Van Vlijmen et al. |
| 8,784,823 | B2 | 7/2014 | Burkly et al. |
| 8,895,010 | B2 | 11/2014 | Nadler et al. |
| 8,981,072 | B2 | 3/2015 | Nadler et al. |
| 9,028,826 | B2 | 5/2015 | Noelle |
| 9,044,459 | B2 | 6/2015 | Perrin et al. |
| 9,228,018 | B2 | 1/2016 | Nadler et al. |
| 10,106,618 | B2 | 10/2018 | Lincecum |
| 10,683,356 | B2 | 6/2020 | Lincecum |
| 11,014,990 | B2 | 5/2021 | Lincecum et al. |
| 11,384,152 | B2 | 7/2022 | Lugovskoy |
| 11,692,040 | B2 | 7/2023 | Lincecum et al. |
| 2001/0018041 | A1 | 8/2001 | Hanna et al. |
| 2004/0006208 | A1 | 1/2004 | Karpusas et al. |

(Continued)

FOREIGN PATENT DOCUMENTS

| | | |
|---|---|---|
| CN | 1441675 | 9/2003 |
| CN | 102119174 | 7/2011 |

(Continued)

OTHER PUBLICATIONS

Pinelli et al. An Anti-CD154 Domain Antibody Prolongs Graft Survival and Induces FoxP3p iTreg in the Absence and Presence of CTLA-4 lg. American Journal of Transplantation 2013; 13: 3021-3030. (Year: 2013).*

Kim et al. Fc-Silent Anti-CD154 Domain Antibody Effectively Prevents Nonhuman Primate Renal Allograft Rejection. Am J Transplant. May 2017; 17(5):1182-1192. (Year: 2017).*

(Continued)

*Primary Examiner* — Maher M Haddad

(74) *Attorney, Agent, or Firm* — Sterne, Kessler Goldstein & Fox P.L.L.C.

(57) ABSTRACT

Anti-human CD40L antibodies engineered to lack the ability to activate platelets and methods for treating patients having a CD40L-associated disease.

11 Claims, 16 Drawing Sheets

Specification includes a Sequence Listing.

(56) References Cited

U.S. PATENT DOCUMENTS

| | | |
|---|---|---|
| 2004/0110226 A1 | 6/2004 | Lazar |
| 2007/0048300 A1 | 3/2007 | Taylor et al. |
| 2007/0190053 A1 | 8/2007 | Kalled et al. |
| 2008/0138349 A1 | 6/2008 | Stavenhagen et al. |
| 2011/0172400 A1 | 7/2011 | Grant et al. |
| 2012/0100166 A1* | 4/2012 | Roschke ............ A61K 47/6845 435/254.2 |
| 2012/0251531 A1 | 10/2012 | Baehner et al. |
| 2013/0045219 A1 | 2/2013 | Burkly |
| 2013/0095109 A1 | 4/2013 | Nadler et al. |
| 2014/0099317 A1 | 4/2014 | Suri et al. |
| 2014/0220031 A1 | 8/2014 | Van Vlijmen et al. |
| 2014/0302016 A1 | 10/2014 | Burkly et al. |
| 2014/0363428 A1 | 12/2014 | Igawa |
| 2015/0104450 A1 | 4/2015 | Minter et al. |
| 2016/0075790 A1 | 3/2016 | Nadler et al. |
| 2016/0207980 A1* | 7/2016 | Du ......................... C07K 16/00 |
| 2017/0051059 A1* | 2/2017 | Suri ................ A61K 39/39541 |
| 2017/0166655 A1 | 6/2017 | Lazar et al. |
| 2023/0048260 A1 | 2/2023 | Lugovskoy |

FOREIGN PATENT DOCUMENTS

| | | | |
|---|---|---|---|
| CN | 103154037 | 6/2013 | |
| WO | WO 95/006481 | 3/1995 | |
| WO | WO 96/040246 | 12/1996 | |
| WO | WO 98/052606 | 11/1998 | |
| WO | WO 99/051258 | 10/1999 | |
| WO | WO 01/083755 | 11/2001 | |
| WO | WO 02/004021 | 1/2002 | |
| WO | WO 02/018445 | 3/2002 | |
| WO | WO 04/037204 | 5/2004 | |
| WO | WO 05/003174 | 1/2005 | |
| WO | WO 05/003175 | 1/2005 | |
| WO | WO 05/011376 | 2/2005 | |
| WO | WO-2005018572 A2 * | 3/2005 | ....... A61K 47/48215 |
| WO | WO 06/029879 | 3/2006 | |
| WO | WO-2006108035 A1 * | 10/2006 | .............. A23L 33/11 |
| WO | WO 06/138316 | 12/2006 | |
| WO | WO 07/059332 | 5/2007 | |
| WO | WO 07/076354 | 7/2007 | |
| WO | WO 08/118356 | 10/2008 | |
| WO | WO 08/143954 | 11/2008 | |
| WO | WO 10/023482 | 3/2010 | |
| WO | WO 10/065819 | 6/2010 | |
| WO | WO 10/085682 | 7/2010 | |
| WO | WO 12/103218 | 8/2012 | |
| WO | WO 12/138768 | 10/2012 | |
| WO | WO 13/033008 | 3/2013 | |
| WO | WO 13/046704 | 4/2013 | |
| WO | WO 13/056068 | 4/2013 | |
| WO | WO 14/163101 | 10/2014 | |
| WO | WO 15/143209 | 9/2015 | |
| WO | WO 14/132101 | 10/2015 | |
| WO | WO 15/164595 | 10/2015 | |
| WO | WO 16/028810 | 2/2016 | |
| WO | WO 16/126702 | 8/2016 | |

OTHER PUBLICATIONS

Suri et al. In vivo and in vitro characterization of domain antibodies (dAbs) targeting CD40 ligand (CD40L). Transplantation, (Sep. 27, 2012) vol. 94, Supp. Suppl. 10S, pp. 111. Abstract No. 1244. (Year: 2012).*
Abcam, "Anti-GAL4 antibody [5C8]," 2012, 2 pages.
Baker et al, 2007, Identification and Removal of Immunogenicity in Therapeutic Proteins, Current Opinion in Drug Discovery & Development, 10(2):219-227.
Bosco et al., "Wild-type and mutant SOD1 share an aberrant Conformation and a common pathogenic pathway in ALS", Nat. Neurosci., 2010, vol. 13, No. 11, pp. 1396-1403.
Building a Better Mouse, MDA/ALS Newsmagazine, Sep. 1, 2010.
Chen et al., "Enhancement and Destruction of Antibody Function by Somatic Mutation: Unequal Occurrence is Controlled by V Gene Combinatorial Associations," EMBO J., 2995, vol. 14, pp. 2784-2794.
Cicchetti et al., 2009, Environmental toxins and Parkinson's disease: what have we learned from pesticide-induced animal models, Trends in Pharmacological Sciences 30:475-483.
Colman, 1994, Effects of amino acid sequence chagnes on antibody-antigen interactions, Research in Immunology 145: 33-36.
Crepeau et al., Aug. 2017, Challenges and opportunities in targeting the CD28/CTLA-4 pathway in transplantation and autoimmunity, Expert Opin Biol Ther., 17(8):10011012.
Daley et al., "Fc-Disabled Anti-Mouse CD40L Antibodies Retain Efficacy in Promoting Transplantation Tolerance," Am J Transplantation, 2008, vol. 8, pp. 2265-2271.
D'Angelo et al., "Many Routes to an Antibody Heavy-Chain CDR3: Necessary, Yet Insufficient, for Specific Binding, Frontiers in Immunology," Frontiers in Immunology, Original Research, Mar. 2018, vol. 9, Article 395 doi:10.3389/immu.2018.00395.
Davis et al., "Abatacept binds to the Fc receptor CD64 but does not mediate complement-dependent cytotoxicity or antibody-dependent cellular cytotoxicity," J. Rheumatol., 2007, vol. 34, No. 11, pp. 2204-2210.
Drachman et al., 1994, Trail of immunosuppression in amyotrophic lateral sclerosis neuro—using total lymphoid irradiation, Annals of Neurology, 35(2).
Dumont et al., "IDEC-131. IDEC/Eisai," Curr Opin Inventing Drugs, 2002, pp. 725-734, vol. 3, No. 5.
Gilliland "Rapid and Reliable Cloning of Antibody Variable Regions and Generation of Recombinant Single Chain Antibody Fragments", Tissue Antigens, 1996, vol. 47, pp. 1-20.
Gruzman et al., "Common Molecular Signature in SOD1 for both Sporadic and Familial Amyotrophic Lateral Sclerosis", PNAS, 2007, vol. 104, No. 30, pp. 12524-12529.
Holgate et al., "Circumventing Immunogenicity in the Development of Therapeutic Antibodies," Idrugs, 2009, vol. 12, No. 4, pp. 233-237.
Imgenex, Monoclonal Antibody to IGF-1R (Clone 24-31), accessed Sep. 21, 2012, 2 pgs.
Jefferis, Mar. 2009, IgG-Fc-mediated effector functions: molecular definition of interaction sites for effector ligands and the role of glycosylation, Nature Reviews/Drug Discovery, 8:226-234.
Kallmeier et al., "Poster—Improvements to the GS System for Easier Re-expression of Human Antibodies," 1 page.
Karpusas et al., "Structure of CD40 Ligand in Complex with the Fab Fragment of a Neutralizing Humanized Antibody," Structure, 2001, vol. 9, No. 4, pp. 321-329.
Ke et al, "CD40-CD40L interactions promote neuronal death in a model of neurodegeneration due to mild impairment of oxidative metabolism", Neurochemistry International, 2005, pp. 204-215, vol. 47, No. 3.
Kiaei et al, "Celastrol blocks neuronal cell death and extends life in transgenic mouse model of amyotrophic lateral sclerosis," Neurodegenerative Diseases, 2005, pp. 246-254, vol. 2, No. 5.
Kirk et al., "CTLA4-Ig and anti-CD40 Ligand Prevent Renal Allograft Rejection in Primates", Proc Natl Acad Sci Neuro—USA, 1997, vol. 94, pp. 8789-8794.
Kiyoshi et al., 2018, Assessing the heterogeneity of the Fc-Glycan of a therapeutic antibody using an engineered FcyReceptor IIIa-immobilized column, Scientific Reports, 8:3955 pp. 1-11.
Knosalla et al., "Initial experience with the human anti-human CD154 monoclonal antibody, ANI793, in pig-to-baboon xenotransplantation", Xenotransplantation, 2004, pp. 353-360, vol. 11, No. 4.
Kussie et al., "a Single Engineered Amino Acid Substitution Changes Antibody Fine Specificity," 1994, J. Immunol., vol. 152, pp. 146-152.
Law et al., "Preclinical Antilymphoma Activity of a Human Anti-CD40 Monoclonal Antibody, SGN-40", Cancer Res, 2005, vol. 65, No. 18, pp. 8331-88338.
Lederman et al., "Identification of a Novel Surface Protein on Activated CD4+ T Cells That Induces Contact-dependent B Cell Differentiation (Help)," J. Exp. Med., 1992, vol. 175, No. 4, pp. 1901-1101.

(56) References Cited

OTHER PUBLICATIONS

Leitner et al., Working with ALS Mice:, The Jackson Laboratory, Oct. 14, 2009.

Lincecum et al., "From Transcriptome Analysis to Therapeutic anti-CD40L Treatment in the SOD1 Model of Amyotrophic Lateral Sclerosis", Nature Genetics, 2010, pp. 1-10.

Linsley et al., "CTLA-4 is a Second Receptor for the B Cell Activation Antigen B7," J. Exp. Med., 1991, vol. 174, No. 3, pp. 561-569.

Ludolph et al., "Guidelines for Preclinical Animal Research in ALS/MND: A Consensus Meeting," Amyotrophic Lateral Sclerosis, 2010, vol. 11, pp. 38-45.

Madsen A., Building a Better Mouse: How Animal Models Help Fight ALS, MDA/ALS Newsmagazine, Sep. 1, 2010, vol. 15, No. 5, 4 pages.

Mirabet et al., 2008, Platelet pro-aggregatory effects of CD40L monoclonal antibody, Molecular Immunology, 45:937-944.

National Institute of Neurological Disorders and Stroke (NINDS), "Amyotrophic Lateral Sclerosis (ALS) Fact Sheet", NIH Internet Publication relating to ALS accessed Nov. 19, 2012, 8 PP.

Needleman et al., 1970, A general method applicable to the search for similarities in the amino acid sequence of two proteins, J. Mol. Biol. 48:444-453.

Okuno et al., "Induction of cyclooxygenase-2 in reactive glial cells by the CD40 pathway: relevance to amyotrophic lateral sclerosis," Journal of Neurochemistry, 2004, vol. 91, No. 2, pp. 404-412.

Piche-Nicholas et al., "Changes in complementarity-determining regions significantly alter IgG binding to the neonatal Fc receptor (FcRN) and pharmacokinetics," MABS, 2018, vol. 10, No. 1, pp. 81-94, oi.org/10.1080/19420862.2017.1389355.

Rudikoff et al., "Single Amino Acid Substitution Altering Antigen-binding Specificity," Proc Natl Acad Sci USA, Mar. 1982, vol. 79, pp. 1979-1983.

Sakoda, Saburou, "Study on a breakthrough technique to diagnosis or treat amyotrophic lateral sclerosis—Analysis of CD40 in amyotrophic lateral sclerosis"—Report of 2006 Houkatsu Kenkyuu, 2007, pp. 51-53 (English translation).

Santa Cruz Biotechnology Inc., accessed Sep. 21, 2012, 1 pg.

Saunders et al., 2019, Conceptual approaches to modulating antibody effector functions and circulating half-life, Frontiers in Immunology, 10:1-20.

Seattle Genetics Receives Key U.S. Patents for SGN-40 Program, Jan. 19, 2005, http://www.seattlegenetics.com/, Posted by MMSupport.net, http://www.mmsupport.net/seattle-genetics-receives-key-Neuro—US-patents-for-sgn-40-program/, 3 pages.

Starzl et al., "Refinements in the Surgical Technique of Liver Transplantation," Semin Liver Dis., 1985, vol. 5, No. 4, pp. 349-356.

Tai et al., "Mechanisms by Which SGN-40, a Humanized Anti-CD40 Antibody, Induces Cytotoxicity in Human Multiple Myeloma Cells: Clinical Implications", Cancer Research, 2004, vol. 64, pp. 2846-2852.

Traynor et al., "Neuroprotective agents for clinical trials in ALS: A systematic assessment," Neurology, 2006, vol. 67, pp. 20-27.

Vainzof et al., "Animal Models for Genetic Neuromuscular Diseases," J. Mol. Neurosci., 2008, pp. 241-248, vol. 34.

Van Blitterswijk et al., "Anti-superoxide Dismutase Antibodies are Associated with Survival in Patients with Sporadic Amyotrophic Lateral Sclerosis", Amyotroph Lateral Scler, 2011, vol. 12, No. 6, pp. 430-438.

Viglietta et al., "CTLA4Ig treatment in patients with multiple sclerosis", Neurology, 2008, pp. 917-924, vol. 71, No. 12.

Wang et al., 2018, IgG Fc engineering to modulate antibody effector functions, Protein Cell, 9:63-73.

Xie et al., "Engineering of a Novel Anti-CD40L Domain Antibody for Treatment of Autoimmune Diseases," J. Immunol., 2014, vol. vol. 192, No. 9, pp. 4083-4092.

Extended European Search Report for EP16747111, dated Jul. 4, 2018, 11 pages.

International Search Report and Written Opinion for PCT Application No. PCT/US2016/016165, dated Jul. 5, 2016, 11 pages.

International Search Report and Written Opinion for PCT/Neuro—US2009/066715, dated Mar. 22, 2010, 11 pages.

Hargreaves, Mar. 31, 2004, Selective depletion of activated T cells: the CD40L-specific antibody experience, Trends in Molecular Medicine, 10(3):130-135.

Zhang et al., May 2008, Effects of anti-CD40L monoclonal antibodies on rejection of rat pancreatic islet xenografts, Chinese J Bases Clin General Surg, 15(5):329-332.

\* cited by examiner

FIG. 1A

Heavy chain hu5c8 (SEQ ID NO: 21)

```
QVQLVQSGAE VVKPGASVKL SCKASGYIFT SYYMYWVKQA PGQGLEWIGE
INPSNGDTNF NEKFKSKATL TVDKSASTAY MELSSLRSED TAVYYCTRSD
GRNDMDSWGQ GTLVTVSSAS TKGPSVFPLA PSSKSTSGGT AALGCLVKDY
FPEPVTVSWN SGALTSGVHT FPAVLQSSGL YSLSSVVTVP SSSLGTQTYI
CNVNHKPSNT KVDKKVEPKS CDKTHTCPPC PAPELLGGPS VFLFPPKPKD
TLMISRTPEV TCVVVDVSHE DPEVKFNWYV DGVEVHNAKT KPREEQYNST
YRVVSVLTVL HQDWLNGKEY KCKVSNKALP APIEKTISKA KGQPREPQVY
TLPPSRDELT KNQVSLTCLV KGFYPSDIAV EWESNGQPEN NYKTTPPVLD
SDGSFFLYSK LTVDKSRWQQ GNVFSCSVMH EALHNHYTQK SLSLSPGK
```

FIG. 1B

Heavy chain JB5 (SEQ ID NO: 9)

```
QVQLVQSGAE VVKPGASVKL SCKASGYIFT SYYMYWVKQA PGQGLEWIGE
INPSNGDTNF NEKFKSKATL TVDKSASTAY MELSSLRSED TAVYYCTRSD
GRNDMDSWGQ GTLVTVSSAS TKGPSVFPLA PSSKSTSGGT AALGCLVKDY
FPEPVTVSWN SGALTSGVHT FPAVLQSSGL YSLSSVVTVP SSSLGTQTYI
CNVNHKPSNT KVDKKVEPKS SDKTHTSPPS PAPELLGGSS VFLFPPKPKD
TLMISRTPEV TCVVVDVSHE DPEVKFNWYV DGVEVHNAKT KPREEQYNST
YRVVSVLTVL HQDWLNGKEY KCKVSNKALP APIEKTISKA KGQPREPQVY
TLPPSRDELT KNQVSLTCLV KGFYPSDIAV EWESNGQPEN NYKTTPPVLD
SDGSFFLYSK LTVDKSRWQQ GNVFSCSVMH EALHNHYTQK SLSLSPGK
```

FIG. 1C

Heavy chain JB5-K74R (SEQ ID NO: 13)

```
QVQLVQSGAE VVKPGASVKL SCKASGYIFT SYYMYWVKQA PGQGLEWIGE
INPSNGDTNF NEKFKSKATL TVDRSASTAY MELSSLRSED TAVYYCTRSD
GRNDMDSWGQ GTLVTVSSAS TKGPSVFPLA PSSKSTSGGT AALGCLVKDY
FPEPVTVSWN SGALTSGVHT FPAVLQSSGL YSLSSVVTVP SSSLGTQTYI
CNVNHKPSNT KVDKKVEPKS SDKTHTSPPS PAPELLGGSS VFLFPPKPKD
TLMISRTPEV TCVVVDVSHE DPEVKFNWYV DGVEVHNAKT KPREEQYNST
YRVVSVLTVL HQDWLNGKEY KCKVSNKALP APIEKTISKA KGQPREPQVY
TLPPSRDELT KNQVSLTCLV KGFYPSDIAV EWESNGQPEN NYKTTPPVLD
SDGSFFLYSK LTVDKSRWQQ GNVFSCSVMH EALHNHYTQK SLSLSPGK
```

FIG. 2A

Light Chain JB5 (SEQ ID NO: 7)

```
DIVLTQSPAT LSVSPGERAT ISCRASQRVS SSTYSYMHWY QQKPGQPPKL
LIKYASNLES GVPARFSGSG SGTDFTLTIS SVEPEDFATY YCQHSWEIPP
TFGGGTKLEI KRTVAAPSVF IFPPSDEQLK SGTASVVCLL NNFYPREAKV
QWKVDNALQS GNSQESVTEQ DSKDSTYSLS STLTLSKADY EKHKVYACEV
THQGLSSPVT KSFNRGEC
```

FIG. 2B

Light Chain JB5-R28K (SEQ ID NO: 11)

```
DIVLTQSPAT LSVSPGEKAT ISCRASQKVS SSTYSYMHWY QQKPGQPPKL
LIKYASNLES GVPARFSGSG SGTDFTLTIS SVEPEDFATY YCQHSWEIPP
TFGGGTKLEI KRTVAAPSVF IFPPSDEQLK SGTASVVCLL NNFYPREAKV
QWKVDNALQS GNSQESVTEQ DSKDSTYSLS STLTLSKADY EKHKVYACEV
THQGLSSPVT KSFNRGEC
```

FIG. 2C

Fc region of hu5c8 (SEQ ID NO: 3)

```
EPKSCDKTHT CPPCPAPELL GGPSVFLFPP KPKDTLMISR TPEVTCVVVD
VSHEDPEVKF NWYVDGVEVH NAKTKPREEQ YNSTYRVVSV LTVLHQDWLN
GKEYKCKVSN KALPAPIEKT ISKAKGQPRE PQVYTLPPSR DELTKNQVSL
TCLVKGFYPS DIAVEWESNG QPENNYKTTP PVLDSDGSFF LYSKLTVDKS
RWQQGNVFSC SVMHEALHNH YTQKSLSLSP GK
```

FIG. 2D

Fc region of JB5 (SEQ ID NO: 4)

```
EPKSSDKTHT SPPSPAPELL GGSSVFLFPP KPKDTLMISR TPEVTCVVVD
VSHEDPEVKF NWYVDGVEVH NAKTKPREEQ YNSTYRVVSV LTVLHQDWLN
GKEYKCKVSN KALPAPIEKT ISKAKGQPRE PQVYTLPPSR DELTKNQVSL
TCLVKGFYPS DIAVEWESNG QPENNYKTTP PVLDSDGSFF LYSKLTVDKS
RWQQGNVFSC SVMHEALHNH YTQKSLSLSP GK
```

FIG. 15

| SEQ ID NO: | Description | Sequence |
|---|---|---|
| 1 | hu5c8 and JB5 VL region | DIVLTQSPATLSVSPGERATISCRASQRVSSSTYSYMHWYQQKPGQPPKL LIKYASNLESGVPARFSGSGSGTDFTLTISSVEPEDFATYYCQHSWEIPP TFGGGTKLEIK |
| 2 | hu5c8 and JB5 VH region | QVQLVQSGAEVVKPGASVKLSCKASGYIFTSYYMYWVKQAPGQGLEWIGE INPSNGDTNFNEKFKSKATLTVDKSASTAYMELSSLRSEDTAVYYCTRSD GRNDMDSWGQGTLVTVSS |
| 3 | Fc region | EPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLN GKEYKCKVSNKALPAPIEKTISKAKGQPREPQVYTLPPSRDELTKNQVSL TCLVKGFYPSDIAVEWESNGQPENNYKTTPPVLDSDGSFFLYSKLTVDKS RWQQGNVFSCSVMHEALHNHYTQKSLSLSPGK |
| 4 | JB5 Fc region | EPKSSDKTHTSPPSPAPELLGGSSVFLFPPKPKDTLMISRTPEVTCVVVD VSHEDPEVKFNWYVDGVEVHNAKTKPREEQYNSTYRVVSVLTVLHQDWLN GKEYKCKVSNKALPAPIEKTISKAKGQPREPQVYTLPPSRDELTKNQVSL TCLVKGFYPSDIAVEWESNGQPENNYKTTPPVLDSDGSFFLYSKLTVDKS RWQQGNVFSCSVMHEALHNHYTQKSLSLSPGK |
| 5 | JB5-R28K VL region | DIVLTQSPATLSVSPGERATISCRASQKVSSSTYSYMHWYQQKPGQPPKL LIKYASNLESGVPARFSGSGSGTDFTLTISSVEPEDFATYYCQHSWEIPP TFGGGTKLEIK |
| 6 | JB5-K74R VH region | QVQLVQSGAEVVKPGASVKLSCKASGYIFTSYYMYWVKQAPGQGLEWIGE INPSNGDTNFNEKFKSKATLTVDRSASTAYMELSSLRSEDTAVYYCTRSD GRNDMDSWGQGTLVTVSS |
| 7 | JB5 light chain Amino acid sequence | DIVLTQSPATLSVSPGERATISCRASQRVSSSTYSYMHWYQQKPGQPPKL LIKYASNLESGVPARFSGSGSGTDFTLTISSVEPEDFATYYCQHSWEIPP TFGGGTKLEIKRTVAAPSVFIFPPSDEQLKSGTASVVCLLNNFYPREAKV QWKVDNALQSGNSQESVTEQDSKDSTYSLSSTLTLSKADYEKHKVYACEV THQGLSSPVTKSFNRGEC |

FIG. 16

| SEQ ID NO: | Description | Sequence |
|---|---|---|
| 8 | JB light chain nucleotide sequence | GACATCGTGCTGACCCAGTCCCCCGCCACCCTGTCCGTGTCCCCCGGCGA GAGGGCCACCATCTCCTGCAGGGCCTCCCAGAGGGTGTCCTCCTCCACCT ACTCCTACATGCACTGGTACCAGCAGAAGCCCGGCCAGCCCCCAAGCTG CTGATCAAGTACGCCTCCAACCTGGAGTCCGGCGTGCCCGCCAGGTTCTC CGGCTCCGGCTCCGGCACCGACTTCACCCTGACCATCTCCTCCGTGGAGC CCGAGGACTTCGCCACCTACTACTGCCAGCACTCCTGGGAGATCCCCCCC ACCTTCGGCGGCGGCACCAAGCTGgaaatcaaaCGTACGGTGGCTGCACC ATCTGTCTTCATCTTCCCGCCATCTGATGAGCAGTTGAAATCTGGAACTG CCTCTGTTGTGTGCCTGCTGAATAACTTCTATCCCAGAGAGGCCAAAGTA CAGTGGAAGGTGGATAACGCCCTCCAATCGGGTAACTCCCAGGAGAGTGT CACAGAGCAGGACAGCAAGGACAGCACCTACAGCCTCAGCAGCACCCTGA CGCTGAGCAAAGCAGACTACGAGAAACACAAAGTCTACGCCTGCGAAGTC ACCCATCAGGGCCTGAGCTCGCCCGTCACAAAGAGCTTCAACAGGGGAGA GTGTTAGTGA |
| 9 | JB5 heavy chain amino acid sequence | QVQLVQSGAEVVKPGASVKLSCKASGYIFTSYYMYWVKQAPGQGLEWIGE INPSNGDTNFNEKFKSKATLTVDKSASTAYMELSSLRSEDTAVYYCTRSD GRNDMDSWGQGTLVTVSSASTKGPSVFPLAPSSKSTSGGTAALGCLVKDY FPEPVTVSWNSGALTSGVHTFPAVLQSSGLYSLSSVVTVPSSSLGTQTYI CNVNHKPSNTKVDKKVEPKSSDKTHTSPPSPAPELLGGSSVFLFPPKPKD TLMISRTPEVTCVVVDVSHEDPEVKFNWYVDGVEVHNAKTKPREEQYNST YRVVSVLTVLHQDWLNGKEYKCKVSNKALPAPIEKTISKAKGQPREPQVY TLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK |

FIG. 17

| SEQ ID NO: | Description | Sequence |
|---|---|---|
| 10 | JB5 heavy chain nucleic acid sequence | CAGGTGCAGCTGGTGCAGTCCGGCGCCGAGGTGGTGAAGCCCGGCGCCTC CGTGAAGCTGTCCTGCAAGGCCTCCGGCTACATCTTCACCTCCTACTACA TGTACTGGGTGAAGCAGGCCCCCGGCCAGGGCCTGGAGTGGATCGGCGAG ATCAACCCCTCCAACGGCGACACCAACTTCAACGAGAAGTTCAAGTCCAA GGCCACCCTGACCGTGGACAAGTCCGCCTCCACCGCCTACATGGAGCTGT CCTCCCTGAGGTCCGAGGACACCGCCGTGTACTACTGCACCAGGTCCGAC GGCAGGAACGACATGGACTCCTGGGGCCAGGGCACCCTGGTGACCGTGTC CTCCGCTAGCACCAAGGGCCCATCGGTCTTCCCCCTGGCACCCTCCTCCA AGAGCACCTCTGGGGGCACAGCAGCCCTGGGCTGCCTGGTCAAGGACTAC TTCCCCGAACCGGTGACGGTGTCGTGGAACTCAGGCGCCCTGACCAGCGG CGTGCACACCTTCCCGGCTGTCCTACAGTCCTCAGGACTCTACTCCCTCA GCAGCGTGGTGACCGTGCCCTCCAGCAGCTTGGGCACCCAGACCTACATC TGCAACGTGAATCACAAGCCCAGCAACACCAAGGTGGACAAGAAAGTTG*g tgagaggccagcacagggagggagggtgtctgctggaagccaggctcagc gctcctgcctggacgcatccggctatgcagcccagtccagggcagcaa ggcaggccccgtctgcctcttcaccggaggcctctgcccgccccactca tgctcaggggagagggtcttctggcttttttcccaggctctgggcaggcac aggctaggtgcccctaacccaggccctgcacacaaaggggcaggtgctgg gctcagacctgccaagagccatatccgggaggaccctgcccctgacctaa gccacccaaaggccaaactctccactccctcagctcggacaccttctc tcctcccagattccagtaactcccaatctttctctgcag*AGCCCAAATC TAGTGACAAAACTCACACAAGCCCACCGAGCCCAG*gtaagccagcccagg cctcgccctccagctcaaggcgggacaggtgcccctagagtagcctgcatc cagggacaggccccagccgggtgctgacacgtccacctccatctcttcct cag*CACCTGAACTCCTGGGGGGATCCTCAGTCTTCCTCTTCCCCCCAAAA CCCAAGGACACCCTCATGATCTCCCGGACCCCTGAGGTCACATGCGTGGT GGTGGACGTGAGCCACGAAGACCCTGAGGTCAAGTTCAACTGGTACGTGG ACGGCGTGGAGGTGCATAATGCCAAGACAAAGCCGCGGGAGGAGCAGTAC AACAGCACGTACCGTGTGGTCAGCGTCCTCACCGTCCTGCACCAGGACTG GCTGAATGGCAAGGAGTACAAGTGCAAGGTCTCCAACAAAGCCCTCCCAG CCCCCATCGAGAAAACCATCTCCAAAGCCAAAG*gtgggaccgtggggtg cgagggccacatggacagaggccggctcggcccaccctctgcctgagag tgaccgctgtaccaacctctgtccctacag*GGCAGCCCCGAGAACCACAG GTGTACACCCTGCCCCCATCCCGGGATGAGCTGACCAAGAACCAGGTCAG CCTGACCTGCCTGGTCAAAGGCTTCTATCCCAGCGACATCGCCGTGGAGT GGGAGAGCAATGGGCAGCCGGAGAACAACTACAAGACCACGCCTCCCGTG CTGGACTCCGACGGCTCCTTCTTCCTCTACAGCAAGCTCACCGTGGACAA GAGCAGGTGGCAGCAGGGGAACGTCTTCTCATGCTCCGTGATGCATGAGG CTCTGCACAACCACTACACACAGAAGAGCCTCTCCCTGTCTCCGGGTAAA *taatga* |

FIG. 18

| SEQ ID NO: | Description | Sequence |
|---|---|---|
| 11 | JB5-R28K light chain amino acid sequence | DIVLTQSPATLSVSPGERATISCRASQKVSSSTYSYMHWYQQKPGQPPKL LIKYASNLESGVPARFSGSGSGTDFTLTISSVEPEDFATYYCQHSWEIPP TFGGGTKLEIKRTVAAPSVFIFPPSDEQLKSGTASVVCLLNNFYPREAKV QWKVDNALQSGNSQESVTEQDSKDSTYSLSSTLTLSKADYEKHKVYACEV THQGLSSPVTKSFNRGEC |
| 12 | JB5-R28K light chain nucleic acid sequence | GACATCGTGCTGACCCAGTCCCCCGCCACCCTGTCCGTGTCCCCCGGCGA GAGGGCCACCATCTCCTGCAGGGCCTCCCAGAAGGTGTCCTCCTCCACCT ACTCCTACATGCACTGGTACCAGCAGAAGCCCGGCCAGCCCCCCAAGCTG CTGATCAAGTACGCCTCCAACCTGGAGTCCGGCGTGCCCGCCAGGTTCTC CGGCTCCGGCTCCGGCACCGACTTCACCCTGACCATCTCCTCCGTGGAGC CCGAGGACTTCGCCACCTACTACTGCCAGCACTCCTGGGAGATCCCCCCC ACCTTCGGCGGCGGCACCAAGCTGgaaatcaaaCGTACGGTGGCTGCACC ATCTGTCTTCATCTTCCCGCCATCTGATGAGCAGTTGAAATCTGGAACTG CCTCTGTTGTGTGCCTGCTGAATAACTTCTATCCCAGAGAGGCCAAAGTA CAGTGGAAGGTGGATAACGCCCTCCAATCGGGTAACTCCCAGGAGAGTGT CACAGAGCAGGACAGCAAGGACAGCACCTACAGCCTCAGCAGCACCCTGA CGCTGAGCAAAGCAGACTACGAGAAACACAAAGTCTACGCCTGCGAAGTC ACCCATCAGGGCCTGAGCTCGCCCGTCACAAAGAGCTTCAACAGGGGAGA GTGTTAGTGA |
| 13 | JB5-K74R heavy chain amino acid | QVQLVQSGAEVVKPGASVKLSCKASGYIFTSYYMYWVKQAPGQGLEWIGE INPSNGDTNFNEKFKSKATLTVDRSASTAYMELSSLRSEDTAVYYCTRSD GRNDMDSWGQGTLVTVSSASTKGPSVFPLAPSSKSTSGGTAALGCLVKDY FPEPVTVSWNSGALTSGVHTFPAVLQSSGLYSLSSVVTVPSSSLGTQTYI CNVNHKPSNTKVDKKVEPKSSDKTHTSPPSPAPELLGGSSVFLFPPKPKD TLMISRTPEVTCVVVDVSHEDPEVKFNWYVDGVEVHNAKTKPREEQYNST YRVVSVLTVLHQDWLNGKEYKCKVSNKALPAPIEKTISKAKGQPREPQVY TLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK |

FIG. 19

| SEQ ID NO: | Description | Sequence |
|---|---|---|
| 14 | JB5-K74R heavy chain nucleic acid sequence | CAGGTGCAGCTGGTGCAGTCCGGCGCCGAGGTGGTGAAGCCCGGCGCCTCCGTGAAGCTGTCCTGCAAGGCCTCCGGCTACATCTTCACCTCCTACTACATGTACTGGGTGAAGCAGGCCCCCGGCCAGGGCCTGGAGTGGATCGGCGAGATCAACCCCTCCAACGGCGACACCAACTTCAACGAGAAGTTCAAGTCCAAGGCCACCCTGACCGTGGACAGGTCCGCCTCCACCGCCTACATGGAGCTGTCCTCCCTGAGGTCCGAGGACACCGCCGTGTACTACTGCACCAGGTCCGACGGCAGGAACGACATGGACTCCTGGGGCCAGGGCACCCTGGTGACCGTGTCCTCCGCTAGCACCAAGGGCCCATCGGTCTTCCCCCTGGCACCCTCCTCCAGAGCACCTCTGGGGGCACAGCAGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAAAGTTG*gtgagaggccagcacaggggagggagggtgtctgctggaagccaggctcagcgctcctgcctggacgcatcccggctatgcagcccagtccagggcagcaaggcaggccccgtctgcctcttcaccggaggcctctgcccgccccactcatgctcaggggagagggtcttctggcttttttcccaggctctgggcaggcacaggctaggtgcccctaacccaggccctgcacacaaaggggcaggtgctgggctcagacctgccaagagccatatccgggaggaccctgcccctgacctaagccacccaaaggccaaactctccactccctcagctcggacaccttctctcctcccagattccagtaactcccaatctttctctgcag*AGCCCAAATCTAGTGACAAAACTCACACAAGCCCACCGAGCCCAG*gtaagccagcccaggcctcgccctccagctcaaggcgggacaggtgcccagagtagcctgcatccagggacaggccccagccgggtgctgacacgtccacctccatctcttcctcag*CACCTGAACTCCTGGGGGGATCCTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGCGGGAGGAGCAGTACAACAGCACGTACCGTGTGGTCAGCGTCCTCACCGTCCTGCACCAGGACTGGCTGAATGGCAAGGAGTACAAGTGCAAGGTCTCCAACAAAGCCCTCCCAGCCCCCATCGAGAAAACCATCTCCAAAGCCAAAG*gtgggaccgtggggtgcgagggccacatggacagaggccggctcggcccaccctctgcctgagagtgaccgctgtaccaacctctgtccctacag*GGCAGCCCCGAGAACCACAGGTGTACACCCTGCCCCCATCCCGGGATGAGCTGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTACAGCAAGCTCACCGTGGACAAGAGCAGGTGGCAGCAGGGGAACGTCTTCTCATGCTCCGTGATGCATGAGGCTCTGCACAACCACTACACACAGAAGAGCCTCTCCCTGTCTCCGGGTAAA*taatga* |

FIG. 20

| SEQ ID NO: | Description | Sequence |
|---|---|---|
| 15 | JB5 CDR-L1 | ISCRASQRVSSSTYSYMH |
| 16 | JB5 CDR-L2 | YASNLES |
| 17 | JB5 CDR-L3 | QHSWEIPPT |
| 18 | JB5 CDR-H1 | SYYMY |
| 19 | JB5 CDR-H2 | EINPSNGDTNFNEKFKS |
| 20 | JB5 CDR-H3 | SDGRNDMDS |
| 21 | Hu5c8 Heavy Chain | QVQLVQSGAEVVKPGASVKLSCKASGYIFTSYYMYWVKQAPGQGLEWIG EINPSNGDTNFNEKFKSKATLTVDKSASTAYMELSSLRSEDTAVYYCTR SDGRNDMDSWGQGTLVTVSSASTKGPSVFPLAPSSKSTSGGTAALGCLV KDYFPEPVTVSWNSGALTSGVHTFPAVLQSSGLYSLSSVVTVPSSSLGT QTYICNVNHKPSNTKVDKKVEPKSCDKTHTCPPCPAPELLGGPSVFLFP PKPKDTLMISRTPEVTCVVVDVSHEDPEVKFNWYVDGVEVHNAKTKPRE EQYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQKS LSLSPGK | ized versions of

SEQUENCE LISTING

```
Sequence total quantity: 25
SEQ ID NO: 1            moltype = AA  length = 111
FEATURE                 Location/Qualifiers
REGION                  1..111
                        note = Synthetically Generated Sequence
source                  1..111
                        mol_type = protein
                        organism = synthetic construct
SEQUENCE: 1
DIVLTQSPAT LSVSPGERAT ISCRASQRVS SSTYSYMHWY QQKPGQPPKL LIKYASNLES    60
GVPARFSGSG SGTDFTLTIS SVEPEDFATY YCQHSWEIPP TFGGGTKLEI K            111

SEQ ID NO: 2            moltype = AA  length = 118
FEATURE                 Location/Qualifiers
REGION                  1..118
                        note = Synthetically Generated Sequence
source                  1..118
                        mol_type = protein
                        organism = synthetic construct
SEQUENCE: 2
QVQLVQSGAE VVKPGASVKL SCKASGYIFT SYYMYWVKQA PGQGLEWIGE INPSNGDTNF    60
NEKFKSKATL TVDKSASTAY MELSSLRSED TAVYYCTRSD GRNDMDSWGQ GTLVTVSS    118

SEQ ID NO: 3            moltype = AA  length = 232
FEATURE                 Location/Qualifiers
REGION                  1..232
                        note = Synthetically Generated Sequence
source                  1..232
                        mol_type = protein
                        organism = synthetic construct
SEQUENCE: 3
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GK          232

SEQ ID NO: 4            moltype = AA  length = 232
FEATURE                 Location/Qualifiers
REGION                  1..232
                        note = Synthetically Generated Sequence
source                  1..232
                        mol_type = protein
                        organism = synthetic construct
SEQUENCE: 4
EPKSSDKTHT SPPSPAPELL GGSSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GK          232

SEQ ID NO: 5            moltype = AA  length = 111
FEATURE                 Location/Qualifiers
REGION                  1..111
```

```
                        note = Synthetically Generated Sequence
source                  1..111
                        mol_type = protein
                        organism = synthetic construct
SEQUENCE: 5
DIVLTQSPAT LSVSPGERAT ISCRASQKVS SSTYSYMHWY QQKPGQPPKL LIKYASNLES    60
GVPARFSGSG SGTDFTLTIS SVEPEDFATY YCQHSWEIPP TFGGGTKLEI K            111

SEQ ID NO: 6            moltype = AA   length = 118
FEATURE                 Location/Qualifiers
REGION                  1..118
                        note = Synthetically Generated Sequence
source                  1..118
                        mol_type = protein
                        organism = synthetic construct
SEQUENCE: 6
QVQLVQSGAE VVKPGASVKL SCKASGYIFT SYYMYWVKQA PGQGLEWIGE INPSNGDTNF    60
NEKFKSKATL TVDRSASTAY MELSSLRSED TAVYYCTRSD GRNDMDSWGQ GTLVTVSS     118

SEQ ID NO: 7            moltype = AA   length = 218
FEATURE                 Location/Qualifiers
REGION                  1..218
                        note = Synthetically Generated Sequence
source                  1..218
                        mol_type = protein
                        organism = synthetic construct
SEQUENCE: 7
DIVLTQSPAT LSVSPGERAT ISCRASQRVS SSTYSYMHWY QQKPGQPPKL LIKYASNLES    60
GVPARFSGSG SGTDFTLTIS SVEPEDFATY YCQHSWEIPP TFGGGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 8            moltype = DNA   length = 660
FEATURE                 Location/Qualifiers
misc_feature            1..660
                        note = Synthetically Generated Sequence
source                  1..660
                        mol_type = other DNA
                        organism = synthetic construct
SEQUENCE: 8
gacatcgtgc tgacccagtc ccccgccacc ctgtccgtgt cccccggcga gagggccacc    60
atctcctgca gggcctccca gagggtgtcc tcctccacct actcctacat gcactggtac   120
cagcagaagc ccggccagcc ccccaagctg ctgatcaagt acgcctccaa cctggagtcc   180
ggcgtgcccg ccaggttctc cggctccggc tccggcaccg acttcaccct gaccatctcc   240
tccgtggagc ccgaggactt cgccacctac tactgccagc actcctggga gatccccccc   300
accttcggcg gcggcaccaa gctggaaatc aaacgtacgg tggctgcacc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc    600
acccatcagg gcctgagctc gcccgtcaca aagagcttca caggggaga gtgttagtga    660

SEQ ID NO: 9            moltype = AA   length = 448
FEATURE                 Location/Qualifiers
REGION                  1..448
                        note = Synthetically Generated Sequence
source                  1..448
                        mol_type = protein
                        organism = synthetic construct
SEQUENCE: 9
QVQLVQSGAE VVKPGASVKL SCKASGYIFT SYYMYWVKQA PGQGLEWIGE INPSNGDTNF    60
NEKFKSKATL TVDKSASTAY MELSSLRSED TAVYYCTRSD GRNDMDSWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS SDKTHTSPPS PAPELLGGSS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSRDELT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGK                                     448

SEQ ID NO: 10           moltype = DNA   length = 1956
FEATURE                 Location/Qualifiers
misc_feature            1..1956
                        note = Synthetically Generated Sequence
source                  1..1956
                        mol_type = other DNA
                        organism = synthetic construct
SEQUENCE: 10
caggtgcagc tggtgcagtc cggcgccgag gtggtgaagc ccggcgcctc cgtgaagctg    60
tcctgcaagg cctccggcta catcttcacc tcctactaca gtgtactggt gaagcaggcc   120
```

-continued

```
cccggccagg gcctggagtg gatcggcgag atcaacccct ccaacggcga caccaacttc    180
aacgagaagt tcaagtccaa ggccaccctg accgtggaca gtccgcctc caccgcctac    240
atggagctgt cctccctgag gtccgaggac cgccgtgt actactgcac caggtccgac     300
ggcaggaacg acatggactc ctggggccag ggcaccctgg tgaccgtgtc ctccgctagc   360
accaagggcc catccgtctt ccccctggca ccctcctcca agagcacctc tgggggcaca   420
gcagccctgg gctgcctggt caaggactac ttccccgaac cggtgacggt gtcgtggaac   480
tcaggcgccc tgaccagcgg cgtgcacacc ttccggctg tcctacagtc ctcaggactc    540
tactccctca gcagcgtggt gaccgtgccc tccagcagct gggcacccca gacctacatc   600
tgcaacgtga atcacaagcc cagcaacacc aaggtggaca agaaagttgg tgagaggcca   660
gcacaggagg ggagggtgtc tgctggaagc caggctcagc gctcctgcct ggacgcatcc   720
cggctatgca gccccagtcc agggcagcaa ggcaggcccc gtctgcctct tcacccggag   780
gcctctgccc gccccactca tgctcaggga gagggtcttc tggcttttc ccaggctct    840
gggcaggcac aggctaggtg cccctaaccc aggccctgca cacaaagggg caggtgctgg   900
gctcagacct gccaagagcc atatccggga ggacctgccc cctgacctaa gcccaccca    960
aaggccaaac tctccactcc ctcagctcgg acaccttctc tcctcccaga ttccagtaac   1020
tcccaatctt ctctctgcag agcccaaatc tagtgacaaa actcacacaa gcccaccgag   1080
cccaggtaag ccagcccagg cctcgccctc cagctcaagg cgggacaggt gccctagagt   1140
agcctgcatc caggggacagg ccccagccgg tgtctgacag gtccacctcc atctcttcct   1200
cagcacctga actcctgggg ggatcctcag tcttcctctt cccccccaaaa cccaaggaca   1260
ccctcatgat ctcccggacc cctgaggtca catgcgtggt ggtggacgtg agccacgaag   1320
accctgaggt caagttcaac tggtacgtgg acggcgtgga ggtgcataat gccaagacaa   1380
agccgcggga ggagcagtac aacagcacgt accgtgtgt cagcgtcctc accgtcctgc   1440
accaggactg gctgaatggc aaggagtaca agtgcaaggt ctccaacaaa gccctcccag   1500
cccccatcga aaaaccatc tccaaagcca aggtgggac ccgtggggtg cgagggccac   1560
atggacagag gccggctcgg cccaccctct gccctgagag tgaccgctgt accaacctct   1620
gtccctacag ggcagccccg agaaccacag tgtaccatcc cgccccatc ccgggatgag   1680
ctgaccaaga accaggtcag cctgacctgc ctggtcaaag gcttctatcc cagcgacatc   1740
gccgtggagt gggagagcaa tgggcagccg gagaacaact acaagaccac gcctcccgtg   1800
ctggactccg acggctcctt cttcctctac agcaagctca ccgtggacaa gagcaggtgg   1860
cagcagggga acgtcttctc atgctccgtg atgcatgagg ctctgcacaa ccactacaca   1920
cagaagagcc tctcccctgtc tccgggtaaa taatga                            1956
```

```
SEQ ID NO: 11        moltype = AA  length = 218
FEATURE              Location/Qualifiers
REGION               1..218
                     note = Synthetically Generated Sequence
source               1..218
                     mol_type = protein
                     organism = synthetic construct
SEQUENCE: 11
DIVLTQSPAT LSVSPGERAT ISCRASQKVS SSTYSYMHWY QQKPGQPPKL LIKYASNLES     60
GVPARFSGSG SGTDFTLTIS SVEPEDFATY YCQHSWEIPP TFGGGTKLEI KRTVAAPSVF    120
IFPPSDEQLK SGTASVVCLL NNFYPREAKV QWKVDNALQS GNSQESVTEQ DSKDSTYSLS    180
STLTLSKADY EKHKVYACEV THQGLSSPVT KSFNRGEC                            218
```

```
SEQ ID NO: 12        moltype = DNA  length = 660
FEATURE              Location/Qualifiers
misc_feature         1..660
                     note = Synthetically Generated Sequence
source               1..660
                     mol_type = other DNA
                     organism = synthetic construct
SEQUENCE: 12
gacatcgtgc tgacccagtc ccccgccacc ctgtccgtgt cccccggcga gagggccacc     60
atctcctgca gggcctccca gaaggtgtcc tcctccacct actcctacat gcactggtac    120
cagcagaagc ccggccagcc ccccaagctg ctgatcaagt acgcctccaa cctggagtc    180
ggcgtgcccg ccaggttctc cggctccggc tccggcaccg acttcaccct gaccatctcc    240
tccgtggagc ccgaggactt cgccacctac tactgccagc actcctggga gatccccccc    300
accttcggcg gcggcaccaa gctggaaatc aaacgtacgg tggctgcacc atctgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca aagtctacgc ctgcgaagtc    600
acccatcagg gcctgagctc gcccgtcaca aagagcttca cagggggaga gtgttagtga    660
```

```
SEQ ID NO: 13        moltype = AA  length = 448
FEATURE              Location/Qualifiers
REGION               1..448
                     note = Synthetically Generated Sequence
source               1..448
                     mol_type = protein
                     organism = synthetic construct
SEQUENCE: 13
QVQLVQSGAE VVKPGASVKL SCKASGYIFT SYYMWVKQA PGQGLEWIGE INPSNGDTNF      60
NEKFKSKATL TVDRSASTAY MELSSLRSED TAVYYCTRSD GRNDMDSWGQ GTLVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS SDKTHTSPPS PAPELLGGSS    240
VFLFPPKPKD TLMISRTPEV TCVVVDVSHE DPEVKFNWYV DGVEVHNAKT KPREEQYNST    300
YRVVSVLTVL HQDWLNGKEY KCKVSNKALP APIEKTISKA KGQPREPQVY TLPPSRDELT    360
```

```
KNQVSLTCLV KGFYPSDIAV EWESNGQPEN NYKTTPPVLD SDGSFFLYSK LTVDKSRWQQ    420
GNVFSCSVMH EALHNHYTQK SLSLSPGK                                      448

SEQ ID NO: 14           moltype = DNA  length = 1956
FEATURE                 Location/Qualifiers
misc_feature            1..1956
                        note = Synthetically Generated Sequence
source                  1..1956
                        mol_type = other DNA
                        organism = synthetic construct
SEQUENCE: 14
caggtgcagc tggtgcagtc cggcgccgag gtggtgaagc ccggcgcctc cgtgaagctg    60
tcctgcaagg cctccggcta catcttcacc tcctactaca tgtactgggt gaagcaggtt    120
cccggccagg gcctggagtg gatcggcgag atcaacccct ccaacggcga caccaacttc    180
aacgagaagt tcaagtccaa ggccaccctg accgtggaca ggtccgcctc caccgcctac    240
atggagctgt cctccctgag gtccgaggac accgccgtgt actactgcac caggtccgac    300
ggcaggaacg acatggactc ctggggccag ggcaccctgg tgaccgtgtc ctccgctagc    360
accaagggcc catcggtctt cccccctgca ccctcctcca agagcacctc tgggggcaca    420
gcagccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcaccca gacctacatc    600
tgcaacgtga atcacaagcc cagcaacacc aaggtggaca agaaagttgg tgagaggcca    660
gcacagggag ggagggtgtc tgctggaagc caggctcagc gctcctgcct ggacgcatcc    720
cggctatgca gccccagtcc agggcagcaa ggcaggcccc gtctgcctct tcacccggag    780
gcctctgccc gccccactca tgctcaggga gagggtcttc tggcttttc cccaggctct    840
gggctgcac aggctaggtg cccctaaccc aggccctgca cacaaagggg caggtgctgg    900
gctcagacct gccaagagcc atatccggga ggacctgcc cctgacctaa gcccacccca    960
aaggccaaac tctccactcc ctcagctcgg acaccttctc tcctcccaga ttccagtaac    1020
tcccaatctt ctctctgcag agcccaaatc tagtgacaaa actcacacaa gcccaccgag    1080
cccaggtaag ccagcccagg cctcgccctc cagctcagg cgggacaggt gccctagagt    1140
agcctgcatc cagggacagg ccccagccgg tgctgacac gtccacctcc atctcttcct    1200
cagcacctga actcctgggg ggatcctcag tcttcctctt ccccccaaaa cccaaggaca    1260
ccctcatgat ctcccggacc cctgaggtca catgcgtggt ggtggacgtg agccacgaag    1320
accctgaggt caagttcaac tggtacgtgg acggcgtgga ggtgcataat gccaagacaa    1380
agccgcggga ggagcagtac aacagcacgt accgtgtggt cagcgtcctc accgtcctgc    1440
accaggactg gctgaatggc aaggagtaca agtgcaaggt ctccaacaaa gccctcccag    1500
cccccatcga gaaaaccatc tccaaagcca aggtgggac ccgtggggtg cgagggccac    1560
atggacagag gccggctcgg cccacccttct gccctgagag tgaccgctgt accaacctct    1620
gtcccctacag ggcagccccg agaaccacag tgtacacctc tgccccatc ccgggatgag    1680
ctgaccaaga accaggtcag cctgacctgc ctggtcaaag gcttctatcc cagcgacatc    1740
gccgtggagt gggagagcaa tgggcagccg gagaacaact acaagaccac gcctcccgtg    1800
ctggactccg acggctcctt cttcctctac agcaagctca ccgtggacaa gagcaggtgg    1860
cagcagggga acgtcttctc atgctccgtg atgcatgagg ctctgcacaa ccactacaca    1920
cagaagagcc tctccctgtc tccgggtaaa taatga                             1956

SEQ ID NO: 15           moltype = AA  length = 18
FEATURE                 Location/Qualifiers
REGION                  1..18
                        note = Synthetically Generated Sequence
source                  1..18
                        mol_type = protein
                        organism = synthetic construct
SEQUENCE: 15
ISCRASQRVS SSTYSYMH                                                 18

SEQ ID NO: 16           moltype = AA  length = 7
FEATURE                 Location/Qualifiers
REGION                  1..7
                        note = Synthetically Generated Sequence
source                  1..7
                        mol_type = protein
                        organism = synthetic construct
SEQUENCE: 16
YASNLES                                                             7

SEQ ID NO: 17           moltype = AA  length = 9
FEATURE                 Location/Qualifiers
REGION                  1..9
                        note = Synthetically Generated Sequence
source                  1..9
                        mol_type = protein
                        organism = synthetic construct
SEQUENCE: 17
QHSWEIPPT                                                           9

SEQ ID NO: 18           moltype = AA  length = 5
FEATURE                 Location/Qualifiers
REGION                  1..5
                        note = Synthetically Generated Sequence
```

```
source                      1..5
                            mol_type = protein
                            organism = synthetic construct
SEQUENCE: 18
SYYMY                                                                           5

SEQ ID NO: 19               moltype = AA   length = 17
FEATURE                     Location/Qualifiers
REGION                      1..17
                            note = Synthetically Generated Sequence
source                      1..17
                            mol_type = protein
                            organism = synthetic construct
SEQUENCE: 19
EINPSNGDTN FNEKFKS                                                             17

SEQ ID NO: 20               moltype = AA   length = 9
FEATURE                     Location/Qualifiers
REGION                      1..9
                            note = Synthetically Generated Sequence
source                      1..9
                            mol_type = protein
                            organism = synthetic construct
SEQUENCE: 20
SDGRNDMDS                                                                       9

SEQ ID NO: 21               moltype = AA   length = 448
FEATURE                     Location/Qualifiers
REGION                      1..448
                            note = Synthetically Generated Sequence
source                      1..448
                            mol_type = protein
                            organism = synthetic construct
SEQUENCE: 21
QVQLVQSGAE VVKPGASVKL SCKASGYIFT SYYMYWVKQA PGQGLEWIGE INPSNGDTNF              60
NEKFKSKATL TVDKSASTAY MELSSLRSED TAVYYCTRSD GRNDMDSWGQ GTLVTVSSAS             120
TKGPSVFPLA PSSKSTSGGT AALGCLVKDY FPEPVTVSWN SGALTSGVHT FPAVLQSSGL             180
YSLSSVVTVP SSSLGTQTYI CNVNHKPSNT KVDKKVEPKS CDKTHTCPPC PAPELLGGPS             240
VFLFPPKPKD TLMISRTPEV TCVVVDVSHE DPEVKFNWYV DGVEVHNAKT KPREEQYNST             300
YRVVSVLTVL HQDWLNGKEY KCKVSNKALP APIEKTISKA KGQPREPQVY TLPPSRDELT             360
KNQVSLTCLV KGFYPSDIAV EWESNGQPEN NYKTTPPVLD SDGSFFLYSK LTVDKSRWQQ             420
GNVFSCSVMH EALHNHYTQK SLSLSPGK                                                448

SEQ ID NO: 22               moltype = AA   length = 374
FEATURE                     Location/Qualifiers
source                      1..374
                            mol_type = protein
                            organism = Homo sapiens
SEQUENCE: 22
MWFLTTLLLW VPVDGQVDTT KAVITLQPPW VSVFQEETVT LHCEVLHLPG SSSTQWFLNG              60
TATQTSTPSY RITSASVNDS GEYRCQRGLS GRSDPIQLEI HRGWLLLQVS SRVFTEGEPL             120
ALRCHAWKDK LVYNVLYYRN GKAFKFFHWN SNLTILKTNI SHNGTYHCSG MGKHRYTSAG             180
ISVTVKELFP APVLNASVTS PLLEGNLVTL SCETKLLLQR PGLQLYFSFY MGSKTLRGRN             240
TSSEYQILTA RREDSGLYWC EAATEDGNVL KRSPELELQV LGLQLPTPVW FHVLFYLAVG             300
IMFLVNTVLW VTIRKELKRK KKWDLEISLD SGHEKKVISS LQEDRHLEEE LKCQEQKEEQ             360
LQEGVHRKEP QGAT                                                               374

SEQ ID NO: 23               moltype = AA   length = 317
FEATURE                     Location/Qualifiers
source                      1..317
                            mol_type = protein
                            organism = Homo sapiens
SEQUENCE: 23
MTMETQMSQN VCPRNLWLLQ PLTVLLLLAS ADSQAAAPPK AVLKLEPPWI NVLQEDSVTL              60
TCQGARSPES DSIQWFHNGN LIPTHTQPSY RFKANNNDSG EYTCQTGQTS LSDPVHLTVL             120
SEWLVLQTPH LEFQEGETIM LRCHSWKDKP LVKVTFFQNG KSQKFSHLDP TFSIPQANHS             180
HSGDYHCTGN IGYTLFSSKP VTITVQVPSM GSSSPMGIIV AVVIATAVAA IVAAVVALIY             240
CRKKRISANS TDPVKAAQFE PPGRQMIAIR KRQLEETNND YETADGGYMT LNPRAPTDDD             300
KNIYLTLPPN DHVNSNN                                                            317

SEQ ID NO: 24               moltype = AA   length = 254
FEATURE                     Location/Qualifiers
source                      1..254
                            mol_type = protein
                            organism = Homo sapiens
SEQUENCE: 24
MWQLLLPTAL LLLVSAGMRT EDLPKAVVFL EPQWYRVLEK DSVTLKCQGA YSPEDNSTQW              60
FHNESLISSQ ASSYFIDAAT VDDSGEYRCQ TNLSTLSDPV QLEVHIGWLL LQAPRWVFKE             120
EDPIHLRCHS WKNTALHKVT YLQNGKGRKY FHHNSDFYIP KATLKDSGSY FCRGLFGSKN             180
```

```
VSSETVNITI TQGLAVSTIS SFFPPGYQVS FCLVMVLLFA VDTGLYFSVK TNIRSSTRDW    240
KDHKFKWRKD PQDK                                                     254

SEQ ID NO: 25           moltype = AA  length = 233
FEATURE                 Location/Qualifiers
source                  1..233
                        mol_type = protein
                        organism = Homo sapiens
SEQUENCE: 25
MWQLLLPTAL LLLVSAGMRT EDLPKAVVFL EPQWYSVLEK DSVTLKCQGA YSPEDNSTQW     60
FHNESLISSQ ASSYFIDAAT VNDSGEYRCQ TNLSTLSDPV QLEVHIGWLL LQAPRWVFKE    120
EDPIHLRCHS WKNTALHKVT YLQNGKDRKY FHHNSDFHIP KATLKDSGSY FCRGLVGSKN    180
VSSETVNITI TQGLAVSTIS SFSPPGYQVS FCLVMVLLFA VDTGLYFSVK TNI           233
```

ANTI-CD40L ANTIBODIES AND METHODS FOR TREATING CD40L-RELATED DISEASES OR DISORDERS

CROSS REFERENCE TO RELATED APPLICATIONS

This application is a divisional application of U.S. patent application Ser. No. 17/322,486, filed on May 17, 2021, which issued as U.S. Pat. No. 11,692,040 on Jul. 4, 2023, which is a divisional application of U.S. patent application Ser. No. 15/931,315, filed May 13, 2020, which issued as U.S. Pat. No. 11,014,990 on May 25, 2021, which is a divisional application of U.S. patent application Ser. No. 16/125,317, filed on Sep. 7, 2018, which issued as U.S. Pat. No. 10,683,356 on Jun. 16, 2020, which is a divisional application of U.S. patent application Ser. No. 15/667,477, filed on Aug. 2, 2017, which issued as U.S. Pat. No. 10,106,618 on Oct. 23, 2018, which is a continuation application of, and claims priority to, PCT International Application No. PCT/US2016/016165, filed Feb. 2, 2016, which claims the benefit under 35 USC § 119 of U.S. Provisional Patent Application No. 62/111,261, filed Feb. 3, 2015, the entire contents of the aforementioned disclosures are hereby incorporated by reference.

FIELD

Anti-CD40L antibodies, compositions comprising the antibodies, and method of using same for treatment of CD40L-related diseases or disorders.

SEQUENCE LISTING

This application contains a Sequence Listing which is submitted herewith in electronically readable format. The electronic Sequence Listing file was created on Jun. 15, 2023 is named "ELDN.007D4.xml" and has a size of 39,961 bytes. The entire content of the Sequence Listing in the electronic "ELDN.007D4.xml" file is incorporated herein by this reference.

BACKGROUND

The interaction of CD40 with its ligand CD40L plays a critical role in regulating immune responses. Binding of CD40L to CD40 triggers activation of the CD40 pathway which up-regulates costimulatory molecules such as CD80 and CD86. Blockade of the interaction between CD40 and CD40L by monoclonal antibodies has been shown to result in protection from autoimmunity and graft rejection in various preclinical models. Recently, in a mouse model of amyotrophic lateral sclerosis, an antibody directed to CD40L was shown to delay disease onset and prolong survival the onset of disease (U.S. Pat. No. 8,435,514, hereby incorporated by reference). In early clinical studies, the humanized anti-CD40L antibody hu5c8 showed efficacy in patients with lupus and in patients with immune thrombocytopenic purpura. However, incidents of thromboembolism in the patients treated with hu5c8 halted further trials. Further in vitro and preclinical animal studies established that interaction of the Fc with the Fc receptor Fc-gamma RIIa caused platelet activation, and aggregation, that resulted in thromboembolic events. Various approaches have been taken to reduce or eliminate the interaction of the immunoglobulin Fc region with Fc-gamma RIIa, including introducing a point mutation in the Fc region to make an alpha-glycosylated anti-IC40L IgG1 which lacked Fc effector function. Other approaches use fragments of antibodies lacking the Fc region or antibodies that contain multiple amino acid substitutions in the Fc region. Although the anti-CD40L antibody, hu5c8, showed efficacy in human patients there is no anti-CD40L antibody on the market. Accordingly, there is a need for improved anti-CD40L antibodies for administration to humans that do not cause platelet activation or aggregation yet are stable and bind to CD40L.

SUMMARY

The present invention provides anti-CD40L antibodies, suitable for use in humans and non-human primates, having an Fc domain that has been engineered to reduce or eliminate platelet aggregation and the concomitant risk of thromboembolism. In one aspect of the invention, the present invention provides antibodies that are humanized versions of the mouse anti-human CD40L antibody 5c8. In one embodiment, an antibody of the present invention comprises a human IgG1 consensus framework wherein the variable light chain and the variable heavy chain comprise the CDR sequences of 5c8.

One aspect of the present invention is an isolated antibody that binds to CD40L and that comprises a light chain and a heavy chain, wherein (i) the light chain comprises a light chain variable region comprising an amino acid sequence having at least 95% sequence identity with SEQ ID NO: 1; (ii) the heavy chain comprises a heavy chain variable region and an Fc region wherein a) the heavy chain variable region comprises an amino acid sequence having at least 95% sequence identity with SEQ ID NO: 2; and b) the Fc region comprises an amino acid sequence having at least 95% sequence identity with SEQ ID NO: 3 wherein the Fc region comprises one or a combination of substitutions selected from the group consisting of C11S, C14S, and P23S. Optionally the Fc region comprises a further amino acid substitution C5S.

Another aspect of the present invention is a method for treating a subject with a CD40L-associated disease or disorder comprising administering to the subject a therapeutically effective amount of an antibody according to the invention. One embodiment of the present invention is a method for treating a subject with a neurodegenerative or neuromuscular disease or disorder, an inflammatory or immune disease or disorder, or an autoimmune disease, comprising administering to the subject a therapeutically effective amount of an antibody according to the invention. Another embodiment is a method for treating a subject with a CD40L-associated disease or disorder comprising administering to the subject a therapeutically effective amount of an antibody according to the invention administered in combination with a compound that blocks the interaction between CD28 and CD86 or between CD28 and CD80.

BRIEF DESCRIPTION OF THE FIGURES

FIGS. 1A, 1B, and 1C show the heavy chain amino acid sequences for hu5c8 (SEQ ID NO: 21) (FIG. 1A), JB5 (SEQ ID NO: 9) (FIG. 1B), and JB5-K74R (SEQ ID NO: 13) (FIG. 1C). The amino acids shown in bold type indicate amino acids that differ between the heavy chain sequences for 5c8 and the heavy chain sequences for JB5 and JB5-K74R.

FIGS. 2A-2D show the light chain amino acid sequence for JB5 (SEQ ID NO: 7) (FIG. 2A), the light chain amino acid sequence for JB5-R28K (SEQ ID NO: 11) (FIG. 2B), the Fc region amino acid sequence for hu5c8 (SEQ ID NO: 3) (FIG. 2C), and the Fc region amino acid sequence for JB5 (SEQ ID NO: 4) (FIG. 2D). The amino acids shown in bold type indicate the amino acids that differ between the light chain sequences for 5c8 and JB5-R28K and between the Fc regions for hu5c8 and JB5.

FIG. 15 provides the variable light region amino acid sequence of the anti-CD40L antibodies JB5 and hu5c8 (SEQ ID NO: 1), the variable heavy region amino acid sequence of the anti-CD40L antibodies JB5 and hu5c8 (SEQ ID NO: 2), the Fc region amino acid sequence of the anti-CD40L antibody hu5c8 (SEQ ID NO: 3), the Fc region amino acid sequence of the anti-CD40L antibody JB5 (SEQ ID NO: 4), the variable light region amino acid sequence of the anti-CD40L antibody JB5-R28K (SEQ ID NO: 5), the variable heavy region amino acid sequence of the anti-CD40L antibody JB5-K74R (SEQ ID NO: 6), and the light chain amino acid sequence of the anti-CD40L antibody JB5 (SEQ ID NO: 7).

FIG. 16 provides the light chain synthetic nucleotide sequence that encodes the anti-CD40L antibody JB5 (SEQ ID NO: 8), upper case letters represent the exons and the lower-case letters represent the intron sequences of the synthetic gene, and also provides the heavy chain amino acid sequence of the anti-CD40L antibody JB5 (SEQ ID NO: 9).

FIG. 17 provides a synthetic nucleic acid sequence that encodes the heavy chain of the anti-CD40L antibody JB5 (SEQ ID NO: 10), uppercase letters represent the exons and the lower-case letters represent the intron sequences of the synthetic gene.

FIG. 18 provides the amino acid sequence of the anti-CD40L antibody JB5-R28K (SEQ ID NO: 11), a synthetic nucleic acid sequence that encodes the light chain of the anti-CD40L antibody JB5-R28K (SEQ ID NO: 12), upper case letters represent the exons and the lower case letters represent the intron sequences of the synthetic gene, and also provides the heavy chain amino acid sequence of the anti-CD40L antibody JB5-K74R (SEQ ID NO: 13).

FIG. 19 provides a synthetic nucleic acid sequence that encodes the heavy chain of the anti-CD40L antibody JB5-K74R (SEQ ID NO: 14) upper case letters represent the exons and the lower-case letters represent the intron sequences of the synthetic gene.

FIG. 20 provides the amino acid sequences of the CDRs of the heavy and light chain of the anti-CD40L antibody JB5: JB5 CDR-L1 (SEQ ID NO: 15), JB5 CDR-L2 (SEQ ID NO: 16), JB5 CDR-L3 (SEQ ID NO: 17), JB5 CDR-H1 (SEQ ID NO: 18), JB5 CDR-H2 (SEQ ID NO: 19), JB5 CDR-H3 (SEQ ID NO: 20) and the amino acid sequence of the hu5C8 heavy chain (SEQ ID NO: 21).

DETAILED DESCRIPTION

Definitions

Figure 3:
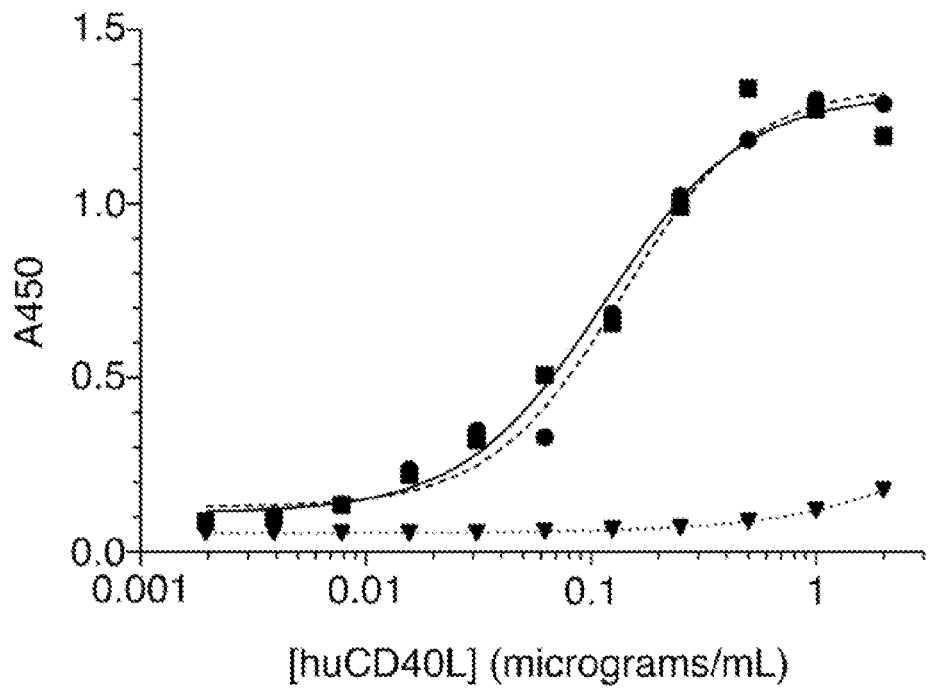
FIG. 3 is a graph showing the relative binding to human CD40L, of JB5 antibody (circles, dotted line), hu5c8 antibody (squares-solid line), and the control CTLA4-IgG1 (triangles).

The terms such as "comprises", "comprised", "comprising", "contains", "containing" and the like have the meaning attributed in United States patent law; these terms are inclusive or open-ended and do not exclude additional, unrecited elements or method steps. Terms such as "consisting essentially of" and "consists essentially of" have the meaning attributed to them in United States patent law; these terms allow for the inclusion of additional ingredients or steps that do not materially affect the basic and novel characteristics of the claim invention. The terms "consists of" and "consisting of" have the meaning ascribed to them in United States patent law; these terms are close ended.

The terms "treat," "treatment" and the like, include therapeutic treatment and prophylactic treatment. Therapeutic treatment is treatment of a subject that has signs or symptoms of the disease, condition, or disorder to be treated. Prophylactic treatments refer to treatment of a subject that is predisposed to the disease, condition or disorder that does not show overt signs of the disease, condition or disorder. Thus, treatment may result in stasis of, partial or total alleviation, or reduction of signs or symptoms of illness, and specifically includes, without limitation, prolongation of survival.

"About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range.

The use of the conjunction "or" is used interchangeably with at "least one of". For example: where a composition comprises A or B, the method must comprise at least one of A and B but may also comprise both A and B. Likewise a composition comprising "A, B, C, or D" must comprise at least one of the groups of A, B, C, and D, but may also comprise all or any combination of A, B, C, and D.

Amino acid substitutions are denoted by the convention in which the original amino acid, the position of the amino acid in the specified sequence and the replacement amino acid are identified, for example, C11S would indicate that the cysteine at position 11 of the polypeptide sequence is replaced with a serine.

"5c8" refers to the mouse anti-human antibody that binds CD40L and is produced by the hybridoma that is available from the ATCC having the accession number HB10916 and is described in U.S. Pat. No. 5,474,771. "hu5c8" refers to a humanized version of 5c8 the sequence of which is disclosed in Karpusas, et al., Structure vol. 9, pp 321-329, (2001).

Reference in the specification is made to percent identity between polypeptide or amino acid sequences. The percent identity between the two sequences is a function of the number of identical positions shared by the sequences, taking into account the number of gaps, and the length of each gap, which need to be introduced for optimal alignment of the two sequences.

Identity can be measured as "local identity" or "global identity". Local identity refers the degree of sequence relatedness between polypeptides as determined by the match between strings of such sequences. Global identity refers to the degree of sequence relatedness of a polypeptide compared to the full-length of a reference polypeptide. Unless specified otherwise, as used herein, identity means global identity. For the purposes of this disclosure, the percentages for global identity are calculated using Needleman and Wunsch ((1970) J. Mol. Biol. 48:444-453) algorithm using a Blossum 62 scoring matrix with a gap penalty of 12, a gap extend penalty of 4, and a frameshift gap penalty of 5. There are many publicly available software programs that incorporate the Needleman and Wunsch algorithm, e.g. the GAP program in the GCG software package.

CD40L is also known as CD154, gp39, T-BAM, 5c8 antigen, or TNF related activation protein (TRAP).

EMBODIMENTS

The present invention provides for therapeutic anti-human CD40L antibodies and methods for using the antibodies of the invention for treating patients with a CD40L-associated disease or disorder. Various exemplary embodiments of the present invention are provided, however, the invention is to be limited by the claims and not the disclosed embodiments.

In one aspect of the invention, the resent invention provides antibodies that are modified versions of the anti-CD40L antibody hu5c8 that comprise a human IgG1 consensus framework having the variable light chain and the variable heavy chain CDR sequences of hu5c8 with an Fe domain modified to prevent platelet activation.

Table 1 provides a description of the SEQ ID NOs referenced in the application.

TABLE 1

| SEQ ID NO: | Description of Sequence |
|---|---|
| 1 | Light chain variable region amino acid sequence (hu5c8 and JBS) |
| 2 | Heavy chain variable region amino acid sequence (hu5c8 and JBS) |
| 3 | Fe region amino acid sequence (hu5c8) |
| 4 | JBS Fe region amino acid sequence |
| 5 | JBS-R28K light chain variable region amino acid sequence |
| 6 | JBS-K74R heavy chain variable region amino acid sequence |
| 7 | JBS light chain amino acid sequence |
| 8 | JBS light chain nucleic acid sequence |
| 9 | JBS heavy chain amino acid sequence |
| 10 | JBS heavy chain nucleic acid sequence |
| 11 | JBS-R28K light chain amino acid sequence |
| 12 | JBS-R28K light chain synthetic gene nucleic acid sequence |
| 13 | JBS-K74R heavy chain amino acid sequence |
| 14 | JBS-K74R heavy chain synthetic gene nucleic acid sequence |
| 15 | CDR-1 of the JBS Variable Light Chain amino acid sequence |
| 16 | CDR-2 of the JBS Variable Light Chain amino acid sequence |
| 17 | CDR-3 of the JBS Variable Light Chain amino acid sequence |
| 18 | CDR-1 of the JBS Variable Heavy Chain amino acid sequence |
| 19 | CDR-2 of the JBS Variable Heavy Chain amino acid sequence |
| 20 | CDR-3 of the JBS Variable Heavy Chain amino acid sequence |
| 21 | Hu5c8 Heavy Chain amino acid sequence |

One embodiment (embodiment A) is an isolated antibody that binds to CD40L and that comprises a light chain and a heavy chain, wherein the light chain comprises a light chain variable region comprising an amino acid sequence having at least 90%, or at least 91%, or at least 92%, or at least 93%, or at least 94%, or at least 95%, or at least 96% or at least 97%, or at least 98% or at least 99% sequence identity with SEQ ID NO: 1 and the heavy chain comprises a variable heavy chain region and an Fe region, wherein the heavy chain variable region comprises an amino acid sequence having at least 90%, or at least 91%, or at least 92%, or at least 93%, or at least 94%, or at least 95%, or at least 96%, or at least 97%, or at least 98%, or at least 99% sequence identity with SEQ ID NO: 2 and the Fe region comprises an amino acid sequence having at least at least 90%, or at least 91%, or at least 92%, or at least 93%, or at least 94%, or at least 95%, or at least 96%, or at least 97%, or at least 98%, or at least 99% sequence identity with SEQ ID NO: 3 wherein the Fe region comprises one or a combination of substitutions selected from the group consisting of C11S, C14S, and P23S.

Another embodiment (embodiment B) is an isolated antibody according to embodiment A, wherein the Fe region further comprises the amino acid substitution C5S.

In variations of the embodiments A and B the antibody comprises a light chain variable region that does not comprise any of the substitutions T33W, S26D, and Q27E.

In other variations of embodiments A and B, the light chain variable region comprises the substitution R28K.

In some variations of the embodiments of A and B, the CDRs of the heavy and light chain have the sequences listed in Table 2.

TABLE 2

| | |
|---|---|
| CDR1 light chain | ISCRASQRVSSSTVSYMH (SEQ ID NO: 15) |
| CDR2 light chain | VASNLES (SEQ ID NO: 16) |
| CDR3 light chain | QHSWEIPPT (SEQ ID NO: 17) |
| CDR1 heavy chain | SVYMY (SEQ ID NO: 18) |
| CDR2 heavy chain | EINPSNGDTNFNEKFKS (SEQ ID NO: 19) |
| CDR3 heavy chain | SDGRNDMDS (SEQ ID NO: 20) |

In yet other variation of embodiments A and B, the light chain variable region comprises the amino acid sequence ICRRASQRVSSSTYSYMH (SEQ ID NO: 15). In still other embodiments, the light chain variable region comprises the amino acid sequence ICRRASQRVSSSTYSYMH (SEQ ID NO: 15) and one or both of the amino acid sequences YASNLES (SEQ ID NO: 16) and QHSWEIPPT (SEQ ID NO: 17).

In some variations of embodiments A and B, the light chain variable region comprises the amino acid sequence of SEQ ID NO: 1. In yet other embodiments the light chain variable region consists of the amino acid of SEQ ID NO: 1. In some embodiments, the light chain consists essentially of the amino acid sequence of SEQ ID NO: 7. In other embodiments, the light chain consists of the amino acid sequence of SEQ ID NO: 7. In still other embodiments, the light chain comprises the amino acid sequence of SEQ ID NO: 11. In yet other embodiments, the light chain consists essentially of the amino acid sequence of SEQ ID NO: 11. In still other embodiments, the light chain consists of the amino acid sequence of SEQ ID NO: 11.

In other variations of the embodiments A and B, the antibody comprises a heavy chain variable region that does not comprise any of the substitutions T30H, Y33W, or S54N. In some embodiments of the antibodies of embodiments A and B, the light chain variable region does not comprise any of the substitutions T33W, S26D, and Q27E. In other variations of embodiments A and B, the light chain variable region does not comprise any of the substitutions T33W, S26D, and Q27E and the heavy chain variable region does not comprise any of the substitutions T30H, Y33W, or S54N.

In yet other variations of the embodiments A and B, the heavy chain variable region comprises the substitution K74R. In one embodiment the heavy chain variable region comprises one or any combination of the amino acid sequences SYYMY (SEQ ID NO: 18), EINPSNGDTNFNEKFKS (SEQ ID NO: 19), and SDGRNDMDS (SEQ ID NO: 20).

In another embodiment, the heavy chain variable region comprises the amino acid sequence of SEQ ID NO: 2. In yet another embodiment the heavy chain variable region consists essentially of the amino acid sequence of SEQ ID NO: 2. In still another embodiment the heavy chain variable region consists of the amino acid sequence of SEQ ID NO: 2. In some embodiments, the heavy chain variable region comprises the amino acid sequence of SEQ ID NO: 6. In yet other embodiments the heavy chain variable region consists essentially of the amino acid sequence of SEQ ID NO: 6. In still other embodiments the heavy chain variable region consists of the amino acid sequence of SEQ ID NO: 6.

One embodiment of the present invention is an isolated antibody, wherein the light chain comprises the amino acid sequence of SEQ ID NO: 1 and the heavy chain consists of the amino acid sequence of SEQ ID NO: 9.

Another embodiment of the present invention is an isolated antibody, wherein the light chain consists of the amino acid sequence of SEQ ID NO: 7 and the heavy chain consists of the amino acid sequence of SEQ ID NO: 9.

Yet another embodiment is an isolated antibody wherein the light chain variable region comprises the amino acid sequence of SEQ ID NO: 5 and the heavy chain consists of the amino acid sequence of SEQ ID NO: 9.

Still another embodiment is an isolated antibody wherein the light chain consists of the amino acid sequence of SEQ ID NO: 11 and the heavy chain consists of the amino acid sequence of SEQ ID NO: 9.

Yet another embodiment, is an isolated antibody wherein the light chain consists of the amino acid sequence of SEQ ID NO: 7 and the heavy chain consists of the amino acid sequence of SEQ ID NO: 13.

Another embodiment is an isolated antibody wherein the light chain consists of the amino acid sequence of SEQ ID NO: 11 and the heavy chain consists of the amino acid sequence of SEQ ID NO: 13.

In preferred embodiments, the antibody of the present invention is stable at 37° C. for a period of at least 12 hours.

In another aspect, the present disclosure provides methods for treating subjects having a CD40L-associated disease or disorder comprising administering to the subject a therapeutically effective amount of an antibody of the present invention. It is contemplated that an antibody of the invention, or mixtures thereof, can be administered to the subject as a monotherapy, which, as used herein, means that the antibody is the only therapeutic agent administered to the patient that is directed to the treatment of the underlying disease or disorder. Monotherapy using an antibody of the invention does not preclude the administration of other drugs, non-limiting examples of which are muscle relaxants, nonsteroidal anti-inflammatory drugs, pain medications, and antidepressants. Accordingly, in various embodiments of the invention, one or a mixture of the antibodies of the invention, is the sole therapeutic agent directed to treatment of the underlying disease or disorder.

It is also contemplated that the antibodies of the invention, or mixtures thereof, can be administered in combination with other therapeutic agents. "In combination with" includes, but is not limited to, administration of the therapeutic agents at different times, at different frequencies, simultaneously, or combined in a single dosage form.

One embodiment is a method for treating a subject with a neurodegenerative or neuromuscular disease or disorder comprising administering to the subject a therapeutically effective amount of an antibody of the present invention. Neurodegenerative or neuromuscular diseases and disorders include, but are not limited to, Alzheimer's Disease, Parkinson's Disease, Amyotrophic Lateral Sclerosis, Multifocal Motor Neuropathy, Primary Lateral Sclerosis, Spinal Muscular Atrophy, Kennedy's Disease, and Spinocerebellar Ataxia.

Another embodiment is a method for treating a subject with Amyotrophic Lateral Sclerosis comprising administering to the subject a therapeutically effective amount of an antibody of the present invention.

One embodiment of the present invention is a method for treating a subject with an inflammatory or immune disease or disorder comprising administering to the subject a therapeutically effective amount of an antibody of the present invention. Inflammatory or immune diseases and disorders include, but are not limited to, colitis, drug induced lupus nephritis, graft versus host disease, transplant rejection and atherosclerosis.

Still another embodiment is a method for treating a subject having an autoimmune disease comprising administering to the subject a therapeutically effective amount of an antibody of the present invention. Autoimmune diseases include, but are not limited to systemic lupus erythematous, type-I diabetes, myasthenia gravis, inflammatory bowel disease, immune thrombocytopenic purpura and rheumatoid arthritis.

Yet another embodiment is method of inhibiting an immune response in a subject comprising administering to the subject a therapeutically effective amount of an antibody of the present invention. In one embodiment the immune response is graft vs. host disease. In another embodiment the immune response is organ transplant rejection.

In some embodiments, an antibody of the present invention is administered as a monotherapy. In one embodiment the antibody is JBS is administered as monotherapy. In another embodiment the antibody JBS-K74R is administered as monotherapy. In yet another embodiment the antibody JBS-R28K is administered as monotherapy. In still another embodiment the antibody JBS-R28K-K74R is administered as monotherapy.

In some embodiments of the methods according to the present invention, the antibody is administered in combination with another therapeutic agent.

In some embodiments, the antibody of the present invention is administered in combination with a compound that blocks the interaction between CD28 and CD86 or between CD28 and CD80.

In some embodiments the compound that blocks the interaction between CD28 and CD86 or between CD28 and CD80 is a CTLA4-Ig fusion protein. In one embodiment the compound that blocks the interaction between CD28 and CD86 or between CD28 and CD80 is abatacept or belatacept or galiximab.

Pharmaceutical Compositions and Methods of Administration

To treat any of the foregoing disorders, pharmaceutical compositions for use in accordance with the methods of the present disclosure may be formulated in a conventional manner using one or more physiologically acceptable carriers. Pharmaceutically acceptable carriers are determined in part by the particular composition being administered, as well as by the particular method used to administer the composition. Accordingly, there are a wide variety of suitable formulations of the compounds useful in the methods of the present disclosure (see, e.g., Remington: The Science and Practice of Pharmacy, 20th ed., Gennaro et al. Eds., Lippincott Williams and Wilkins, 2000).

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

According to the present disclosure the compounds can be administered by any suitable means, which can vary, depending on the type of disorder being treated and on the nature of the compound itself. For example, for the antibodies of the present invention, administration mutes preferably include parenteral, e.g., intramuscular, intravenous, intraarterial, intraperitoneal, or subcutaneous. Preferably, the parenteral dosing is given by injection, most preferably intravenous, intramuscular or subcutaneous injection. The amount to be administered will depend on a variety of factors such as the clinical symptoms, weight of the individual, and whether other drugs are administered. It should be appreciated that determination of proper dosage forms, dosage amounts, and mutes of administration is within the level of ordinary skill in the pharmaceutical and medical arts.

EXAMPLES

The following examples illustrate the methods used to make and test the antibodies of the invention. Suitable modifications and adaptations of the described conditions and parameters normally encountered in the art of molecular biology and immunology will be apparent to one of skill in the art.

Example 1: Antibody Production

In order to produce the antibodies of the invention, nucleic acid sequences encoding the heavy chain and the light chain of the desired antibody were designed to be suitable for expression in mammalian cells such as Chinese Hamster Ovary (CHO) cells. The nucleic acids were then artificially synthesized and ligated into the antibody expression vector BPJPuro using standard molecular biology techniques. BPJPuro is a dual gene mammalian expression vector optimized for selectable and stable expression of immunoglobulins in Chinese Hamster Ovary (CHO) cells. The vector is then transfected into CHO cells and stable transfectants selected.

Production of JBS Antibodies

A nucleic acid (SEQ ID NO: 10) encoding a heavy chain having the amino acid sequence of SEQ ID NO: 9, and a nucleic acid (SEQ ID NO: 8) encoding a light chain having the amino acid sequence of SEQ ID NO: 7, were synthesized and ligated into the antibody expression vector BPJPuro.

The resulting expression vector encoding the heavy and light chains was transfected into the CHO line (CHO SA, Cellectis SA, Paris, France) using liposome mediated transfection.

Stable transfectants were isolated by puromycin selection and subcloned to provide clonal cell lines. Candidate cell lines were adapted to serum free suspension culture and screened for IgG production and robust growth. One of the cell lines was selected and named JBS, the cell line was cultured in a pilot scale bioreactor and the antibody JBS was purified from conditioned medium by sequential concentration, Protein A/G affinity chromatography, and size exclusion chromatography.

Example 2: CD40L Binding Assay

A three part sandwich ELISA assay was used to determine binding kinetics of the JBS antibody relative to the parental antibody hu5c8. All washes were performed using 3 washes of 250 µl of PBS. A 96-well polystyrene plate was coated with 100 µl/well of JBS or hu5c8 antibody (2 µg/ml) for 16 hours at 4° C. The plate was washed and then blocked with 2% bovine serum albumin/PBS for 1 hour at room temperature. The plate was washed and recombinant human CD40L protein (Santa Cruz Biotechnology, Santa Cruz, California, USA) was added to the plate titrated out by 2-fold dilution starting at 2000 ng/ml. After binding and washing, the bound CD40L protein was detected using 100 µl a biotinylated goat anti-human CD40L polyclonal antibody (200 ng/ml) and 100 μl a streptavidin-horseradish peroxidase conjugate at 100 ng/ml. Colorimetric detection was performed with the chromagen TMB (3,3',5,5'-tetramethylbenzidine) and spectrophotometric analysis of absorption at 450 nm The resulting binding curves (FIG. 3) show that JBS (circle) has highly similar CD40L binding relative to the parental antibody hu5c8 (square). The control protein CTLA4-IgG1 (triangle), having the same Fe domain as JBS showed no significant binding. The calculated EC50 for hu5c8 and JBS is 114 and 137 nM, respectively. JB5-R28K and JB5-K74R showed binding similar to that of JBS.

Figure 4:
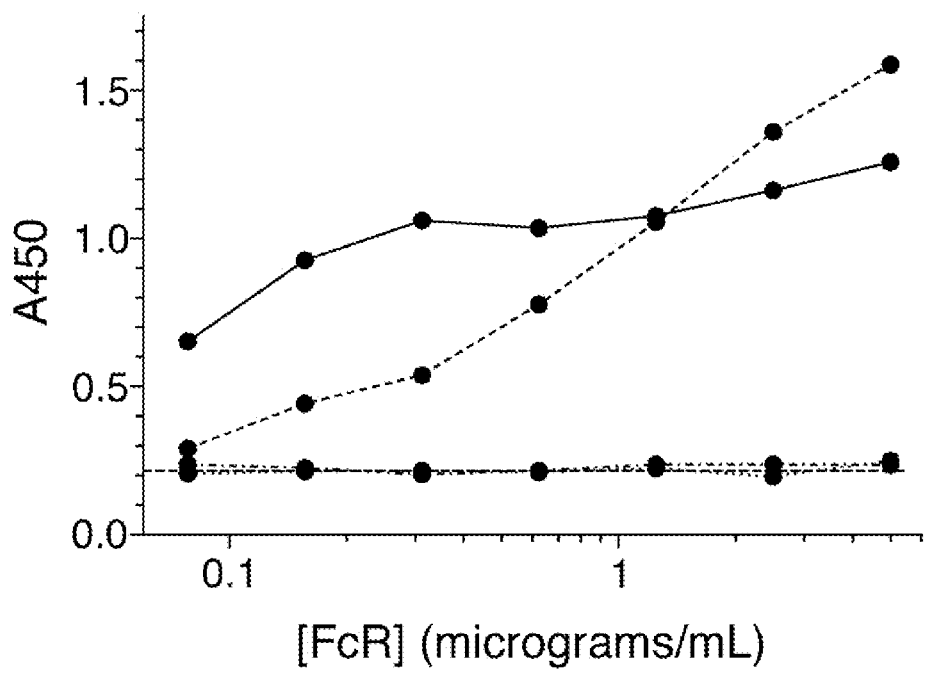
FIG. 4 is a graph showing the binding of hu5c8 antibody to FCGR1A (circle, solid line) (SEQ ID NO: 22), FCGR2A (circle, dotted line) (SEQ ID NO: 23), FCR3A (SEQ ID NO: 24) and FCR3B (SEQ ID NO: 25) isoforms of the human Fc gamma receptor protein.

Example 3: Fe Gamma Receptor Binding Assays hu5c8/Human Fe Gamma Receptor Binding Assay A solid phase ELISA binding assay was performed to determine the level of binding of four human Fe gamma receptor isoforms to the parental hu5c8 antibody. 100 μl/well hu5c8 antibody (2 μg/ml in phosphate buffered saline) was added to the wells of a 96 well polystyrene plate and incubated for 16 hours at 4° C. The plate was blocked and recombinant human Fe gamma receptor (FCGR) proteins (Santa Cruz Biotechnology, Santa Cruz, California) titrated by 2-fold dilution with a starting concentration of 5 μg/ml. Four recombinant FCGR isoforms were tested separately as follows: high affinity Fc region of IgG receptor IA (FCGR1A) (CD64) (SEQ ID NO: 22), low affinity immunoglobulin gamma fc region receptor IIA (FCGR2A) (CD32) (SEQ ID NO: 23), low affinity immunoglobulin gamma fc region receptor IIIA (FCGR3A) (CD16a) (SEQ ID NO: 24), low affinity immunoglobulin gamma fc region receptor IIIB (FCGR3B) (CD16b) (SEQ ID NO: 25). After binding and washing, the FCGR was detected using an appropriate FCGR isoform specific murine monoclonal antibody (1000 ng/ml) and a horseradish peroxidase conjugate goat anti-mouse IgG detector antibody. Colorimetric detection was performed with the chromagen TMB (3,3',5,5'-tetramethylbenzidine) and spectrophotometric analysis of absorption at 450 nm The resulting binding curves (FIG. 4) demonstrate that the parental hu5c8 antibody binds the high affinity FCGR1A (circle, solid line) receptor (SEQ ID NO: 22) and the FCGR2A receptor (SEQ ID NO: 23) (circle, dotted line) expressed on activated platelets, with high affinity. The hu5c8 antibody showed no binding to the FCGR3A receptor (SEQ ID NO: 24) or FCGR3B receptor (SEQ ID NO: 25) isoforms.

JBS-Human Fe Gamma Receptor Binding Assay

Figure 5:
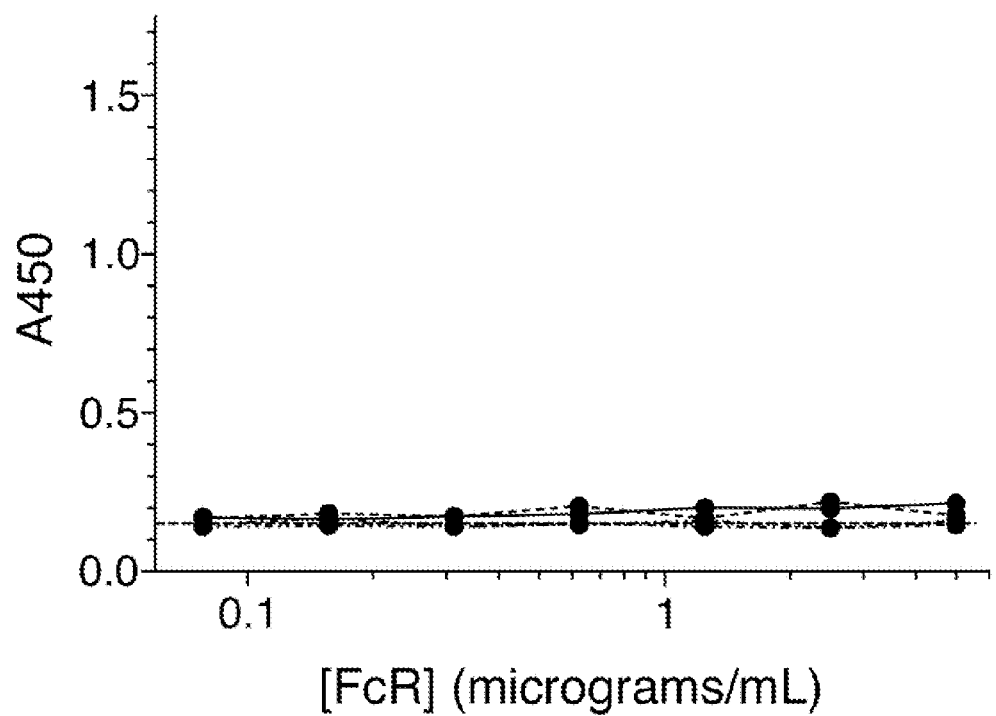
FIG. 5 is a graph showing that JB5 antibody to FCGR1A (SEQ ID NO: 22), FCGR2A (SEQ ID NO: 23), FCR3A (SEQ ID NO: 24), or FCR3B (SEQ ID NO: 25) isoforms of the human Fc gamma receptor protein.

A solid phase binding assay was used to test binding of human Fe gamma receptor isoforms to the mutant JBS antibody. 100 μl/well JBS (2 μg/ml in phosphate buffered saline) was coated for 16 hours onto a 96 well polystyrene plate. The plate was blocked and recombinant human Fe gamma receptor (FCGR) proteins (Santa Cruz Biotechnology, Santa Cruz, California) titrated onto by 2-fold dilution with a starting concentration of 5 μg/ml. Four recombinant FCGR isoforms were tested separately as follows: FCGR1A (CD64) (SEQ ID NO: 22), FCGR2A (CD32) (SEQ ID NO: 23), FCGR3A (CD16a) (SEQ ID NO: 24), FCGR3B (CD16b) (SEQ ID NO: 25). After binding and washing the FCGR was detected using an appropriate FCGR isoform specific murine monoclonal antibody (1000 ng/ml) and a horseradish peroxidase conjugate goat anti-mouse IgG detector antibody. Colorimetric detection was performed with the chromagen TMB (3,3',5,5'-tetramethylbenzidine) and spectrophotometric analysis of absorption at 450 nm The resulting binding curves (FIG. 5) demonstrate that the JBS antibody binds neither the high affinity FCGR1A receptor (SEQ ID NO: 22) nor the FCGR2A receptor (SEQ ID NO: 23), expressed on activated platelets, in this assay. Like the parental hu5c8 antibody, no binding was observed for FCGR3A receptor (SEQ ID NO: 24) or FCGR3B receptor (SEQ ID NO: 25).

Example 4: Stability of JBS at 22° C. and at 37° C.

Because JBS lacks three of the disulfide linkages in wild-type IgG1 antibodies, JBS was tested using size exclusion chromatography to determine if the antibody was stable, i.e., existed as a tetrameric, fully intact antibody. Hu5c8, which has the three disulfide linkages was used as a control.

Figure 6:
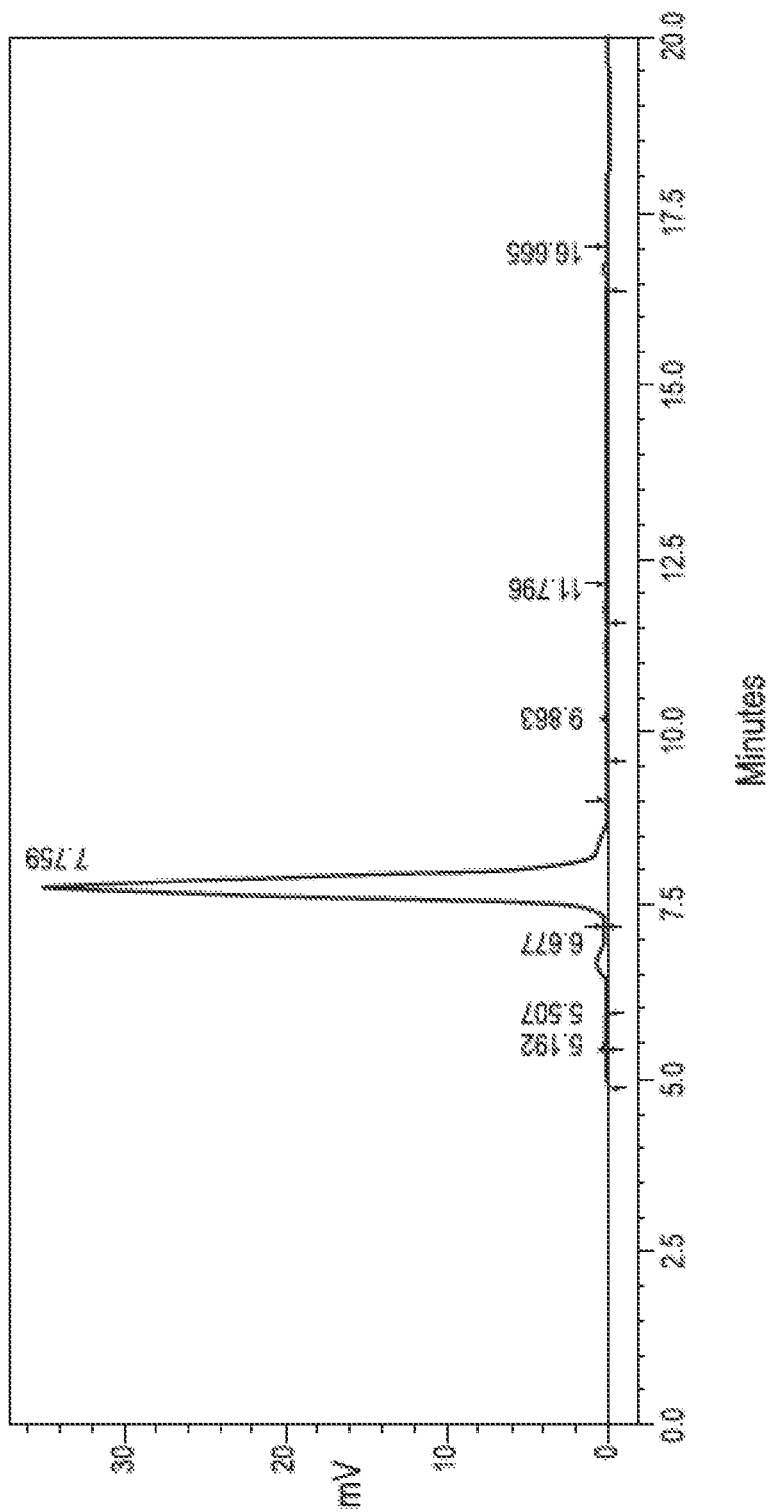
FIG. 6 shows the analytical chromatography elution profile for JB5 antibody run at 30° C. from a size exclusion column.
Figure 7:
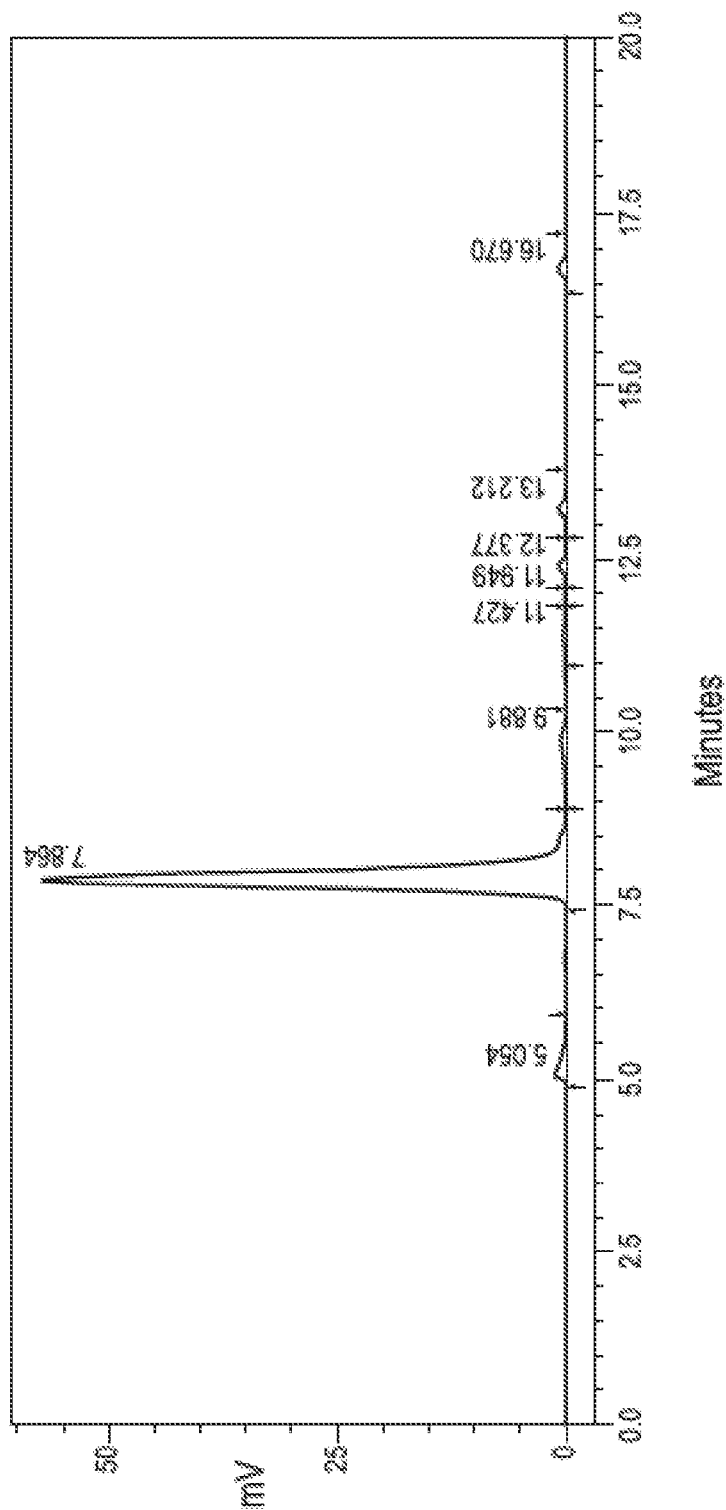
FIG. 7 shows the analytical chromatography elution profile for hu5c8 antibody run at 30° C. from a size exclusion column.

Two experiments were performed, each comparing JBS with hu5c8. In the first experiment, the antibodies were at room temperature (22° C.) before and during chromatography. To simulate in vivo conditions, in the second experiment the antibodies were incubated in human plasma at 37° C. for 30 minutes prior to chromatography at 30° C. Twenty micrograms of JBS or hu5c8 in PBS was injected into a TSK® gel G3000SW (7.8 mm×30 cm, 5 μm bead column) equipped with a pre-column filter TSK® gel Guard SW xl, (6.0 mm×4.0 cm, 7 μm bead column) (Tosoh Bioscience, King of Prussia, PA). The mobile phase was PBS and the elution rate was 1.0 mL/minute and the absorbance was measured at 280 nm. At both 22° C. and at 30° C. JBS had an observed molecular weight of 183 kDa (FIG. 6) and hu5c8 (FIG. 7) had a MW of 164 kDa consistent with the antibody being in the tetrameric, divalent form. The observed 19 kDa difference between the hu5c8 antibody and JBS may be due to increased glycosylation of the Fe domain of JBS.

Example 5: Elimination of Platelet Activation

In order to determine the effect of JBS on CD40L immune complex mediated platelet activation, the antibody was assayed for its ability to induce the platelet cell surface marker protein PAC-1. Whole blood was drawn from three healthy volunteers into 3.2% Na citrate tubes discarding the first 2 ml. Platelet rich plasma was prepared by centrifugation for 15 minutes at 120 g the platelet count was normalized with phosphate buffered saline to $1 \times 10^5$ cells/ml. Immune complexes of recombinant human CD40L (Santa Cruz Biotechnology, Santa Cruz, CA, USA) and the test antibodies, hu5c8, JBS, and hu5c8 F(ab')2 were prepared at a CD40L:Antibody molar ratio of 3:1 (0.6944 nmole CD40L:0.2315 nmole antibody) by preincubation at room temperature for 15 minutes. The immune complex mixture was diluted to a final concentration of 5 μg/ml CD40L in the normalized PBS/platelet solution and incubated at 37° C. for 30 minutes. Negative controls were untreated platelets and CD40L alone. The platelet activation positive control was prepared by the addition of ADP to a final concentration of 20 micromolar in the normalized PBS-platelet solution. After 30 minutes of incubation, anti-human PAC-1-FITC conjugated antibody was added to all samples and incubated for 15 minutes.

Samples were diluted 1:1 into 2% paraformaldehyde:PBS buffer, fixed on ice for 30 minutes, centrifuged at 100 g, for 5 minutes to pellet the cells. The cells were resuspended in PBS. Fluorescence activated cell sorting (FACS™) was performed on a Guava easyCyte™ flow cytometer (EMD Millipore, Inc., Billerica, MA, USA). Post-acquisition analysis was performed using FlowJo™ software (FlowJo, LLC, Ashland, OR, USA).

Figure 8:
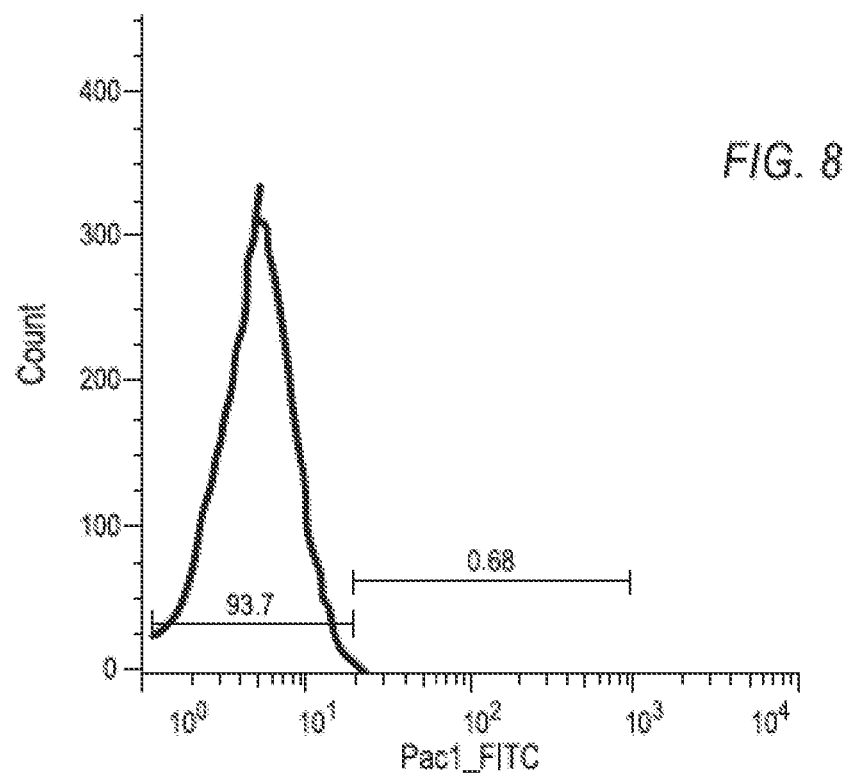
FIG. 8 is a graph showing the binding of the platelet activation marker PAC1 antibody to untreated platelet samples (negative control), as assessed by fluorescence activated cell sorting (FACS).
Figure 9:
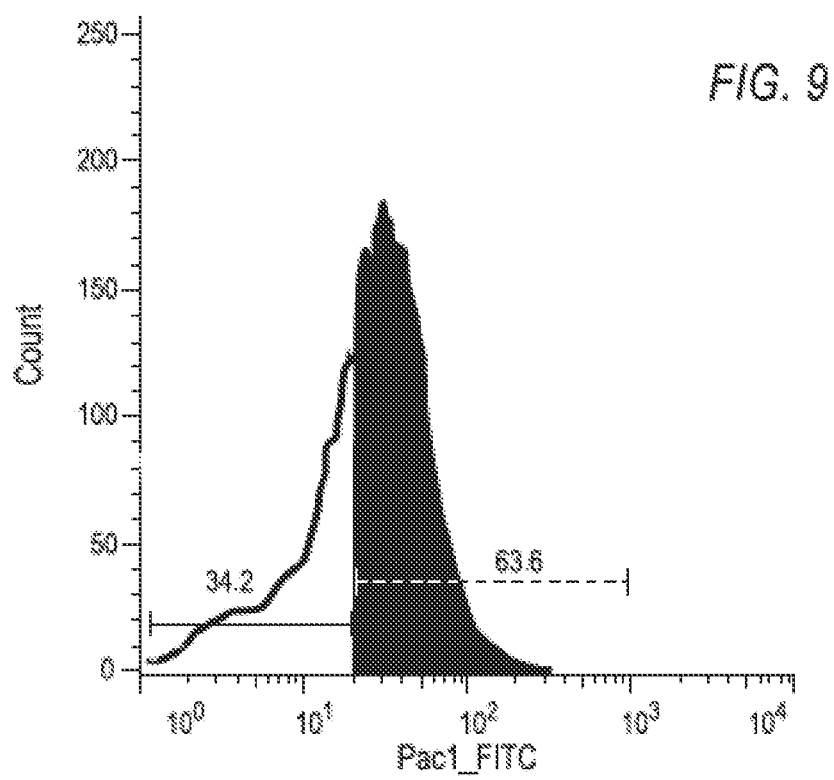
FIG. 9 is a graph showing the binding, as assessed by FACS, of an anti-PAC1 antibody.
Figure 10:
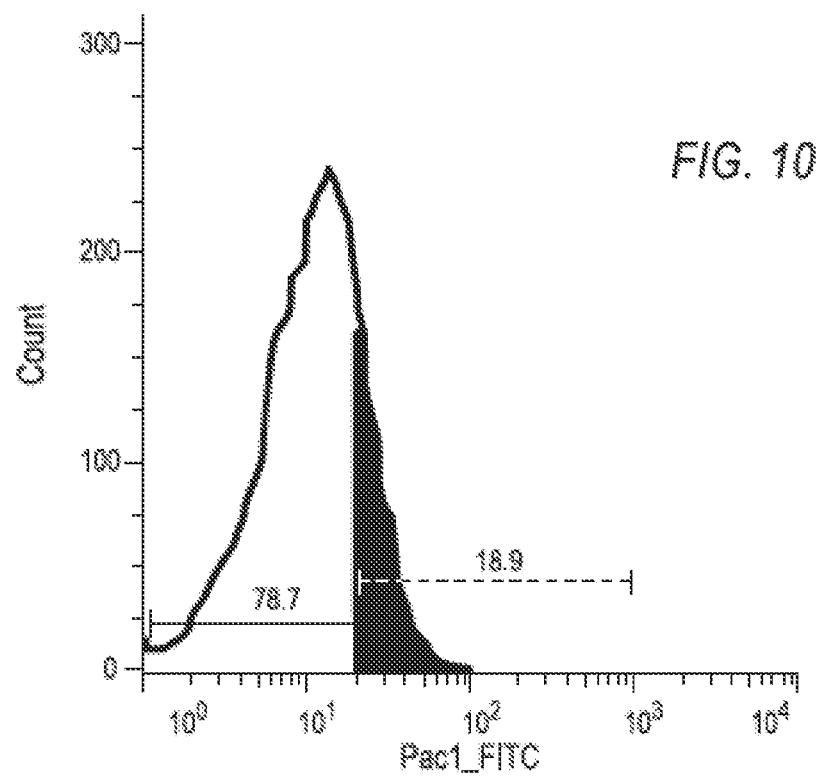
FIG. 10 is a graph showing the binding, as assessed by FACS, of an anti-PAC1 antibody to platelets after the incubation of the platelets with CD40L.
Figure 11:
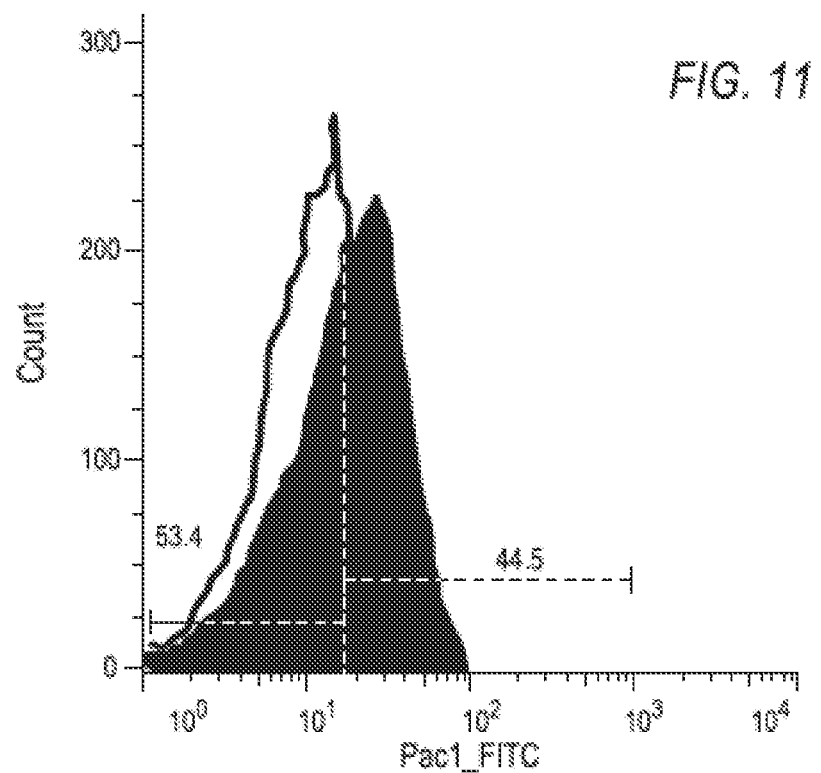
FIG. 11 is a graph showing the binding, as assessed by FACS, of an anti-PAC1 antibody to platelets after incubation of the platelets with an immune complex of CD40L and hu5c8 antibody.
Figure 12:
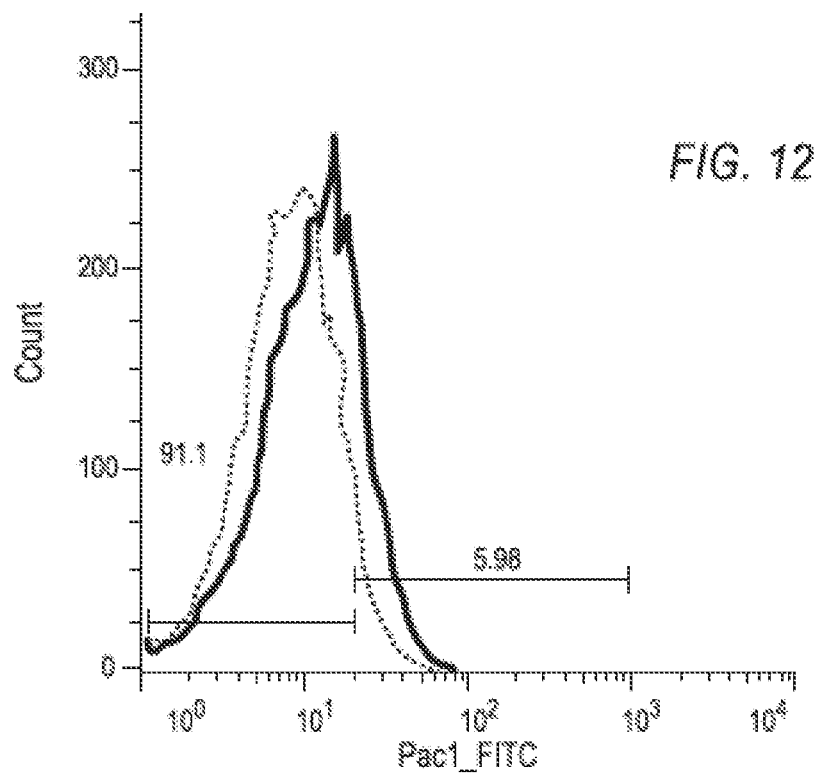
FIG. 12 is a graph showing the binding, as assessed by FACS, of an anti-PAC1 antibody to platelets after incubation of the platelets with an immune complex of CD40L and JB5 antibody.
Figure 13:
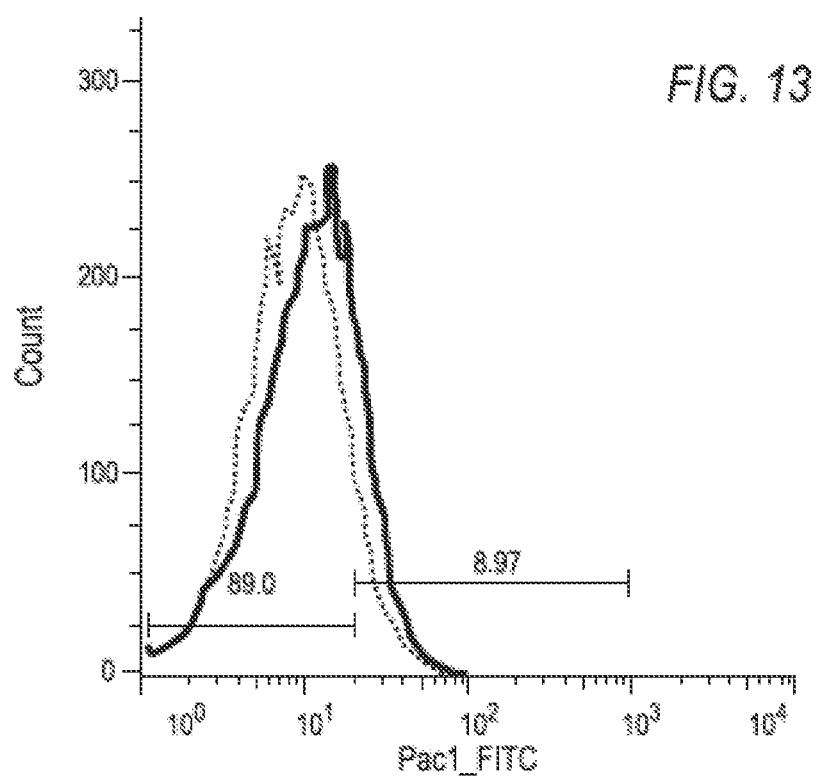
FIG. 13 is a graph showing the binding, as assessed by FACS, of an anti-PAC1 antibody to platelets after incubation of the platelets with an immune complex of CD40L and the hu5c8 F(ab')$_2$.
Figure 14:
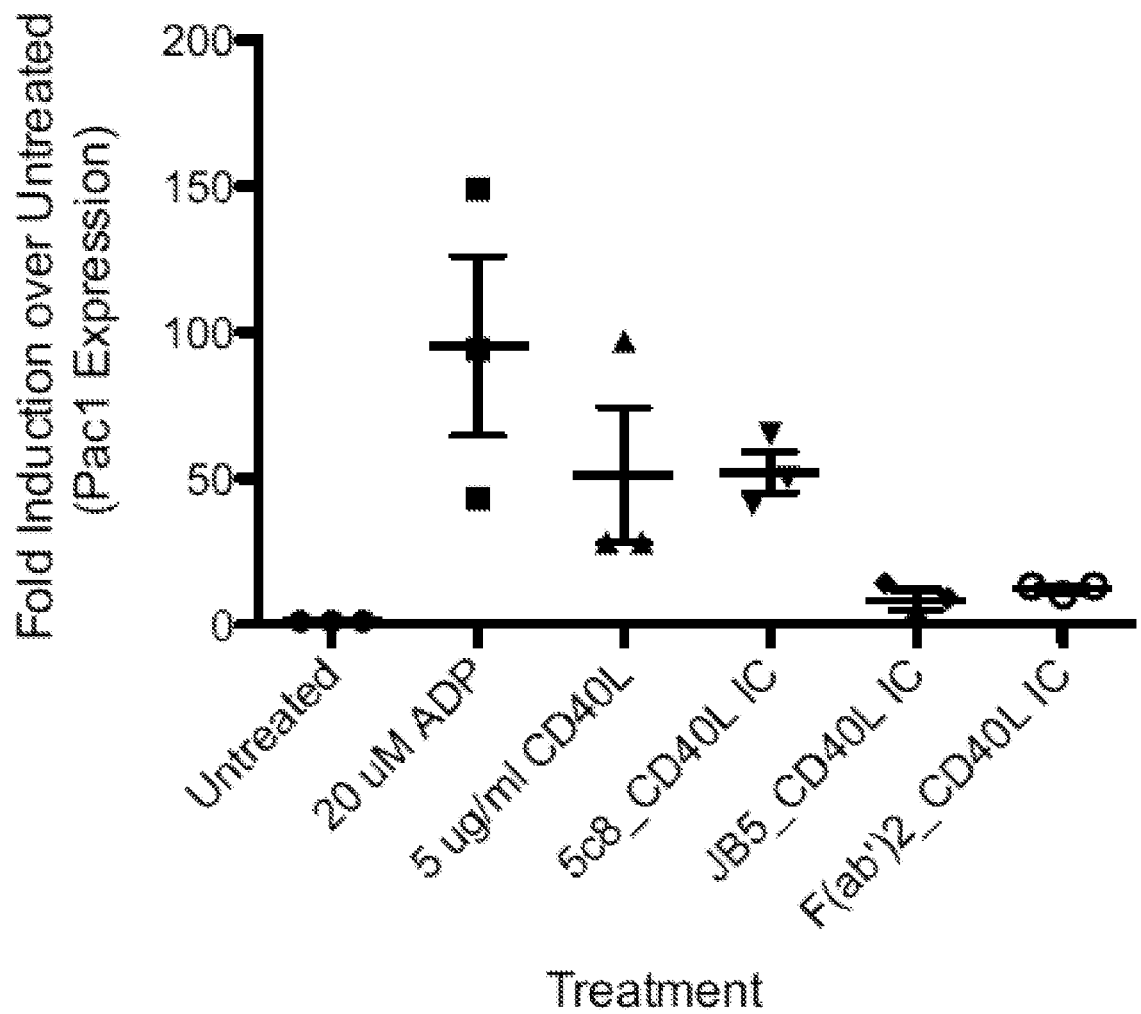
FIG. 14 is a scatter plot graph showing FACS results from three persons' platelets after incubation of the platelets with 20 μM ADP, 5 μg/ml CD40L, the immune complex of CD40L and hu5c8, the immune complex of CD40L and JB5 antibody or the immune complex of CD40L with hu5c8 F(ab')$_2$.

An untreated platelet control sample was used to set negative and positive PAC-1 activation gates (FIG. 8). Platelets activated with 20 micromolar ADP had a significant increase in PAC-1 cell surface expression (FIG. 9). Consistent with published observations, see e.g., Mirabet, M., et al., Molecular Immunology 45, 937-944 (2008), CD40L alone was able to activate platelets at a low level (FIG. 10). This activation was significantly increased when CD40L was present with hu5c8 antibody as an immune complex (FIG. 11). In contrast, the engineered antibody JBS complexed with CD40L demonstrated very low levels of platelet activation (FIG. 12). This reduction in the activation potential of a CD40L:JB5 immune complex is mediated by the loss of FcR interaction because the hu5c8 F(ab')2:CD40L immune complex (FIG. 13) also did not activate platelets relative to the hu5c8-IgG1:CD40L immune complex (FIG. 11). FIG. 14 shows the platelet activation results from three persons' platelets after incubation of the platelets with 20 μM ADP, 5 μg/ml CD40L, the immune complex of CD40L and hu5c8, the immune complex of CD40L and JBS antibody or the immune complex of CD40L with hu5c8 F(ab')2. The JBS immune complex showed no significant platelet activation when compared to the immune complex of CD40L with hu5c8 F(ab')2 platelets ($p<0.34$ (Unpaired T test, 2 tailed; t=1.013, df=4). Further, the JBS immune complex showed significantly less platelet activation when compared with the hu5c8 immune complex ($p<0.005$ (Unpaired T test, 2 tailed; t=S.586, df=4).

While a number of embodiments of this disclosure are described, it is apparent that the basic examples may be altered by one skilled in the art to provide other embodiments that use or encompass methods and processes of this invention. The embodiments and examples are for illustrative purposes and are not to be interpreted as limiting the disclosure, but rather, the appended claims define the scope of this invention.

What is claimed is:

1. A method for treating a subject with a CD40L associated disease or disorder comprising administering to the subject a therapeutically effective amount of an isolated antibody comprising: (a) a light chain and a heavy chain, wherein the light chain comprises a light chain variable region and the heavy chain comprises a heavy chain variable region; and (b) an Fc region consisting of the amino acid sequence of SEQ ID NO:4; wherein
   (i) the light chain variable region consists of the amino acid sequence of SEQ ID NO:1; and the heavy chain variable region consists of the amino acid sequence of SEQ ID NO:2; or
   (ii) the light chain variable region consists of the amino acid sequence of SEQ ID NO:1; and the heavy chain variable region consists of the amino acid sequence of SEQ ID NO:6; or
   (iii) the light chain variable region consists of the amino acid sequence of SEQ ID NO:5; and the heavy chain variable region consists of the amino acid sequence of SEQ ID NO:2; or
   (iv) the light chain variable region consists of the amino acid sequence of SEQ ID NO5; and the heavy chain variable region consists of the amino acid sequence of SEQ ID NO: 6;
   wherein the disease or disorder is a neurodegenerative or neuromuscular disease or disorder, an inflammatory or immune disease or disorder, or an autoimmune disease.

2. The method of claim 1, wherein the disease or disorder is selected from the group consisting of: Alzheimer's Disease, Parkinson's Disease, amyotrophic lateral sclerosis, atherosclerosis, drug induced lupus nephritis, colitis, graft versus host disease, immune thrombocytopenia purpura, inflammatory bowel disease, Kennedy's Disease, Multifocal Motor Neuropathy, myasthenia gravis, Primary Lateral Sclerosis, rheumatoid arthritis, Spinal Muscular Atrophy, Spinocerebellar Ataxia, systemic lupus erythematous, transplant rejection, and type1 diabetes.

3. The method of claim 1, wherein the Fc region consists of the amino acid sequence of SEQ ID NO:4, and the light chain variable region consists of the amino acid sequence of SEQ ID NO:1, and the heavy chain variable region consists of the amino acid sequence of SEQ ID NO:2.

4. The method of claim 1, wherein the antibody is administered in combination with a compound, wherein the compound is a CTLA4-Ig fusion protein, abatacept, belatacept, or galiximab.

5. A method for treating a subject with a CD40L associated disease or disorder comprising administering to the subject a therapeutically effective amount of an isolated antibody comprising: (a) a light chain and a heavy chain, wherein the light chain comprises a light chain variable region and the heavy chain comprises a heavy chain variable region; and (b) an Fc region consisting of the amino acid sequence of SEQ ID NO:4; wherein
   (i) the light chain variable region consists of the amino acid sequence of SEQ ID NO:1; and the heavy chain variable region consists of the amino acid sequence of SEQ ID NO:2; or
   (ii) the light chain variable region consists of the amino acid sequence of SEQ ID NO:1; and the heavy chain variable region consists of the amino acid sequence of SEQ ID NO:6; or
   (iii) the light chain variable region consists of the amino acid sequence of SEQ ID NO:5; and the heavy chain variable region consists of the amino acid sequence of SEQ ID NO:2; or
   (iv) the light chain variable region consists of the amino acid sequence of SEQ ID NO:5; and the heavy chain variable region consists of the amino acid sequence of SEQ ID NO: 6; and
   wherein the light chain comprises the CDR1 of SEQ ID NO: 15;
   wherein the light chain comprises the CDR2 of SEQ ID NO: 16;
   wherein the light chain comprises the CDR3 of SEQ ID NO: 17;
   wherein the heavy chain comprises the CDR1 of SEQ ID NO: 18;
   wherein the heavy chain comprises the CDR2 of SEQ ID NO: 19; and
   wherein the heavy chain comprises the CDR3 of SEQ ID NO: 20; and
   wherein the disease or disorder is a neurodegenerative or neuromuscular disease or disorder, an inflammatory or immune disease or disorder, or an autoimmune disease.

6. The method of claim 5, wherein the disease or disorder is selected from the group consisting of: Alzheimer's Disease, Parkinson's Disease, amyotrophic lateral sclerosis, atherosclerosis, drug induced lupus nephritis, colitis, graft versus host disease, immune thrombocytopenia purpura, inflammatory bowel disease, Kennedy's Disease, Multifocal Motor Neuropathy, myasthenia gravis, Primary Lateral Sclerosis, rheumatoid arthritis, Spinal Muscular Atrophy, Spinocerebellar Ataxia, systemic lupus erythematous, transplant rejection, and type-1 diabetes.

7. The method of claim 5, wherein the Fc region consists of the amino acid sequence of SEQ ID NO:4, and the light chain variable region consists of the amino acid sequence of SEQ ID NO:1, and the heavy chain variable region consists of the amino acid sequence of SEQ ID NO:2.

8. The method of claim 5, wherein the antibody is administered in combination with a compound, wherein the compound is a CTLA4-Ig fusion protein, abatacept, belatacept, or galiximab.

9. A method of inhibiting an immune response in a subject comprising administering to the subject a therapeutically effective amount of an isolated antibody a therapeutically effective amount of an isolated antibody comprising: (a) a light chain and a heavy chain, wherein the light chain comprises a light chain variable region and the heavy chain comprises a heavy chain variable region; and (b) an Fc region consisting of the amino acid sequence of SEQ ID NO:4; wherein
- (i) the light chain variable region consists of the amino acid sequence of SEQ ID NO:1; and the heavy chain variable region consists of the amino acid sequence of SEQ ID NO:2; or
- (ii) the light chain variable region consists of the amino acid sequence of SEQ ID NO:1; and the heavy chain variable region consists of the amino acid sequence of SEQ ID NO:6; or
- (iii) the light chain variable region consists of the amino acid sequence of SEQ ID NO:5; and the heavy chain variable region consists of the amino acid sequence of SEQ ID NO:2; or
- (iv) the light chain variable region consists of the amino acid sequence of SEQ ID NO:5; and the heavy chain variable region consists of the amino acid sequence of SEQ IDNO: 6.

10. The method of claim 9, wherein the Fc region consists of the amino acid sequence of SEQ ID NO:4, and the light chain variable region consists of the amino acid sequence of SEQ ID NO:1, and the heavy chain variable region consists of the amino acid sequence of SEQ ID NO:2.

11. The method of claim 9, wherein the antibody is administered in combination with a compound, wherein the compound is a CTLA4-Ig fusion protein, abatacept, belatacept, or galiximab.

* * * * *